(12) United States Patent
Breen

(10) Patent No.: US 8,820,325 B2
(45) Date of Patent: Sep. 2, 2014

(54) BYMIXER APPARATUS AND METHOD FOR FAST-RESPONSE, ADJUSTABLE MEASUREMENT OF MIXED GAS FRACTIONS IN VENTILATION CIRCUITS

(75) Inventor: Peter H. Breen, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 269 days.

(21) Appl. No.: 12/874,630

(22) Filed: Sep. 2, 2010

(65) Prior Publication Data

US 2011/0082380 A1 Apr. 7, 2011

Related U.S. Application Data

(63) Continuation-in-part of application No. 10/530,602, filed as application No. PCT/US03/33072 on Oct. 14, 2003, now Pat. No. 7,793,659.

(60) Provisional application No. 60/417,892, filed on Oct. 11, 2002.

(51) Int. Cl.
*A61M 16/00* (2006.01)
*A61M 15/00* (2006.01)

(52) U.S. Cl.
USPC ............................. 128/204.18; 128/200.24

(58) Field of Classification Search
USPC ............ 128/200.24, 203.12–204.18, 204.21, 128/201.13, 911
See application file for complete search history.

(56) References Cited

U.S. PATENT DOCUMENTS

| 2,119,446 | A | * | 5/1938 | Sholes ..................... 128/203.13 |
| 3,592,191 | A | | 7/1971 | Jackson |
| 3,913,607 | A | * | 10/1975 | Price .............................. 137/271 |
| 3,977,432 | A | * | 8/1976 | Vidal ............................. 137/889 |
| 4,206,754 | A | | 6/1980 | Cox et al. |
| 4,211,239 | A | | 7/1980 | Raemer et al. |
| 4,352,408 | A | * | 10/1982 | Hardt et al. ................... 181/249 |
| 4,371,053 | A | * | 2/1983 | Jones ............................ 181/249 |
| 4,446,942 | A | * | 5/1984 | Hardt et al. ................... 181/249 |
| 4,619,269 | A | | 10/1986 | Cutler et al. |
| 4,643,272 | A | * | 2/1987 | Gaffrig ......................... 181/260 |
| 4,834,214 | A | * | 5/1989 | Feuling ......................... 181/249 |
| 4,848,333 | A | * | 7/1989 | Waite ........................ 128/205.11 |
| 5,007,420 | A | * | 4/1991 | Bird ........................... 128/200.14 |
| 5,072,737 | A | | 12/1991 | Goulding |
| 5,239,994 | A | | 8/1993 | Atkins |
| 5,318,556 | A | * | 6/1994 | Avallone et al. .............. 604/410 |
| 5,423,313 | A | | 6/1995 | Olsson et al. |

(Continued)

OTHER PUBLICATIONS

Rosenbaum, A. and Breen, P.H., "Novel, adjustable, clinical bymixer measures mixed expired gas concentrations in anesthesia circle circuit," Anesth. Analg. Nov. 2003, 97(5): 1414-20.

(Continued)

*Primary Examiner* — Annette Dixon
(74) *Attorney, Agent, or Firm* — Stout, Uxa, Buyan & Mullins, LLP; Robert D. Buyan

(57) ABSTRACT

Bymixer devices and methods for sampling or obtaining data from mixed respiratory gases in a ventilation circuit. Respiratory gasses from a plurality of consecutive breaths become mixed within a mixing chamber of the bymixer and samples or data are obtained from such mixed respiratory gasses. Optionally, the volume of the mixing chamber and/or the resistance to flow into or through the mixing chamber may be selectable or adjustable.

44 Claims, 11 Drawing Sheets

(56) References Cited

U.S. PATENT DOCUMENTS

| | | | |
|---|---|---|---|
| 5,555,880 A | 9/1996 | Winter et al. | |
| 5,602,368 A * | 2/1997 | Kaneso | 181/255 |
| 5,605,148 A | 2/1997 | Jones | |
| 5,701,883 A | 12/1997 | Hete et al. | |
| 5,722,449 A | 3/1998 | Heinonen et al. | |
| 5,752,506 A | 5/1998 | Richardson | |
| 5,890,490 A | 4/1999 | Aylsworth et al. | |
| 5,967,141 A | 10/1999 | Heinonen | |
| 6,014,890 A | 1/2000 | Breen | |
| 6,196,222 B1 | 3/2001 | Heinonen et al. | |
| 6,253,767 B1 * | 7/2001 | Mantz | 128/205.13 |
| 6,279,574 B1 | 8/2001 | Richardson et al. | |
| 6,298,848 B1 | 10/2001 | Skog | |
| 6,341,663 B1 * | 1/2002 | Alex et al. | 181/249 |
| 6,408,848 B1 | 6/2002 | Feldman et al. | |
| 6,571,796 B2 | 6/2003 | Banner et al. | |
| 6,648,832 B2 | 11/2003 | Orr et al. | |
| 6,752,240 B1 * | 6/2004 | Schlagenhaft | 181/249 |
| 6,955,661 B1 * | 10/2005 | Herweck et al. | 604/264 |
| 2001/0041861 A1 * | 11/2001 | Gobel | 604/99.01 |

OTHER PUBLICATIONS

Breen, Peter H. and Serina, Eugene R., "Bymixer Provides On-line Calibration of Measurement of CO2 Volume Exhaled per Breath," Annals of Biomedical Engineering, vol. 25, pp. 164-171, 1997.

Sanjo, Yoshimitsu, MS and Ikeda, Kazuyuki, M.D., "A Small Bypass Mixing Chamber for Monitoring Metabolic Rate and Anesthetic Uptake: The Bymixer," Journal of Clinical Monitoring, vol. 3 No. 4, Oct. 1987.

* cited by examiner

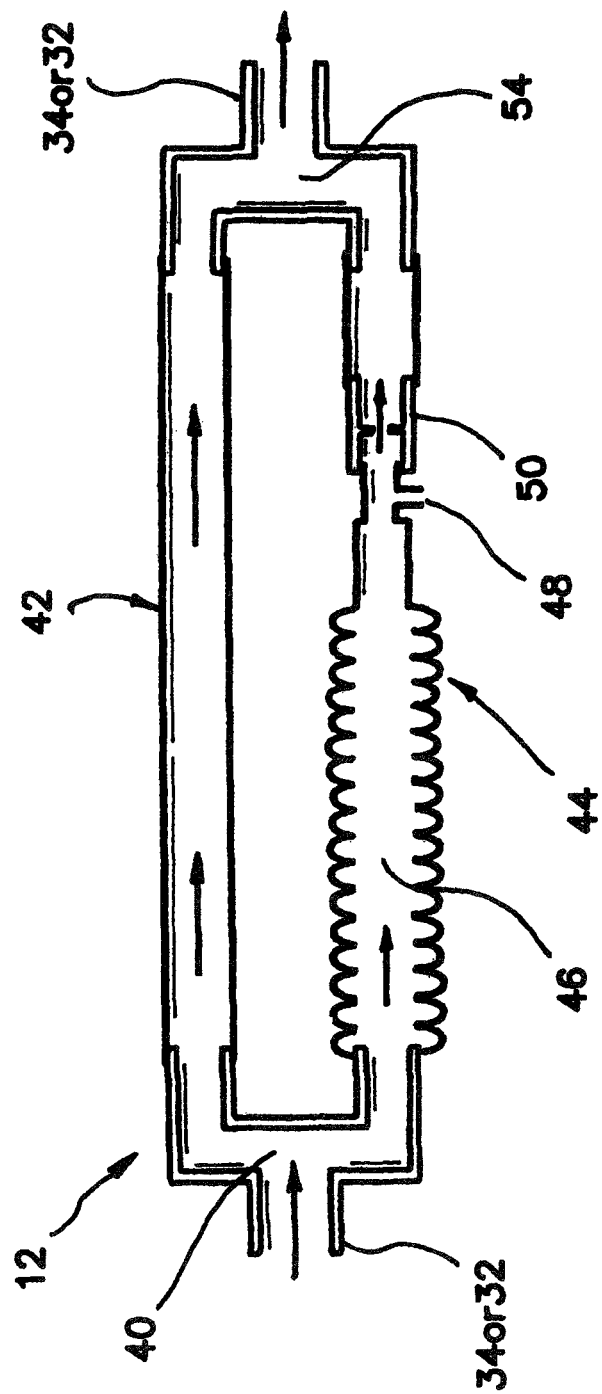

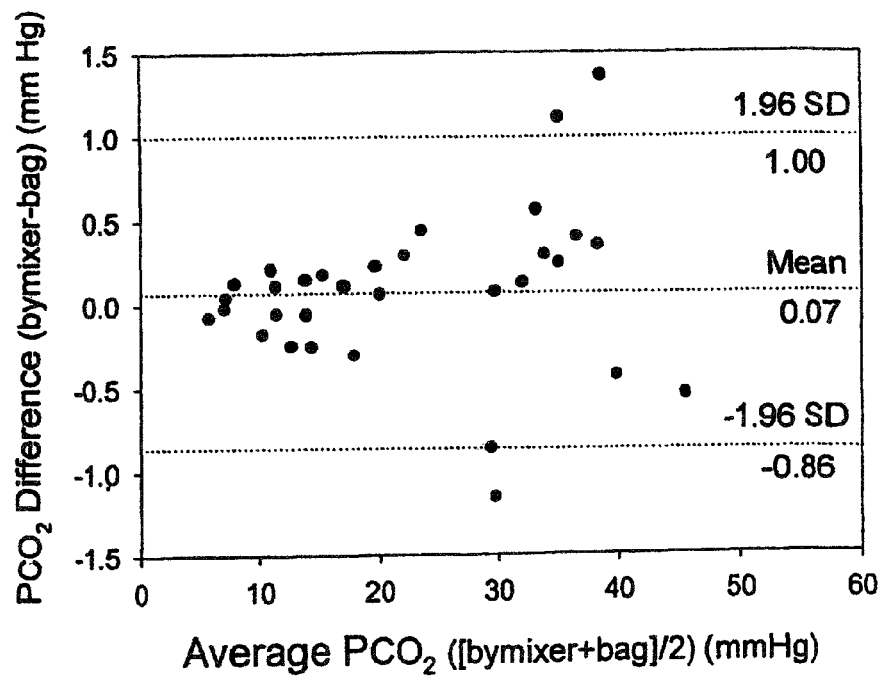
FIG. 4A
FIG. 4B
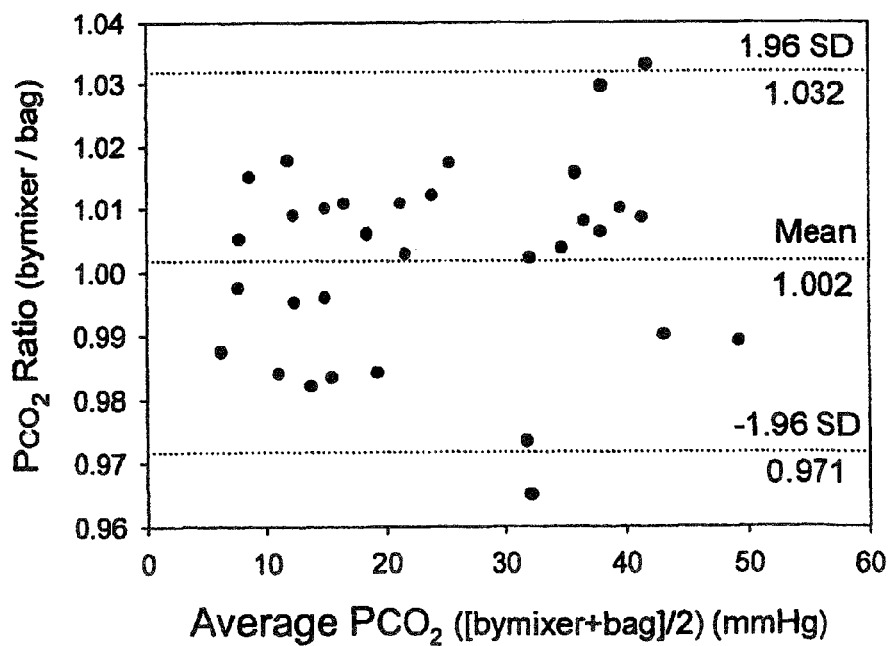

BYMIXER APPARATUS AND METHOD FOR FAST-RESPONSE, ADJUSTABLE MEASUREMENT OF MIXED GAS FRACTIONS IN VENTILATION CIRCUITS

RELATED APPLICATIONS

This is a continuation in part of U.S. patent application Ser. No. 10/530,602 filed Nov. 14, 2005, which is a 35 U.S.C. §371 national stage application of PCT/US03/33072 filed Oct. 14, 2003, which claims priority to U.S. Provisional Patent Application Ser. No. 60/417,892 entitled "Bymixer Apparatus for Fast-Response, Adjustable measurement of Mixed Expired Gas Fractions in the Anesthesia Circle Circuit and Related Method" filed on Oct. 11, 2002, the entire disclosure of each such application being expressly incorporated herein by reference.

STATEMENT REGARDING FEDERALLY SPONSORED RESEARCH OR DEVELOPMENT

This invention was made with government support under grant R01 HL-42637 awarded by the National Institute of Health. The government has certain rights in the invention.

FIELD OF THE INVENTION

The present invention relates generally to biomedical devices and methods, and more particularly to devices and methods for anesthesia, critical care medicine, ventilation and monitoring of pulmonary function.

BACKGROUND OF THE INVENTION

Carbon dioxide ($CO_2$) is normally produced in the tissues of the human body where it becomes dissolved in the blood. The $CO_2$ is then transported in blood to the lung where it diffuses across alveolar membranes and is expelled from the lungs during exhalation.

The term "capnography" refers generally to the measurement of $CO_2$ in airway gas during the ventilation cycle. In patients who are undergoing anesthesia or mechanical ventilation, capnography is sometimes used to measure the partial pressure of $CO_2$ ($PCO_2$) at the airway opening during the ventilation cycle. During the inspiratory phase of the ventilation cycle (i.e., inhalation), a flow of inspired respiratory gas passes through the airway opening. Such inspired respiratory gas typically contains little or no $CO_2$. Thus, during the inspiratory phase, the capnograph obtains an inspiratory baseline $PCO_2$ measurement of zero. During the second phase of the ventilation cycle (expiratory upstroke), alveolar gas from the respiratory bronchioles and alveoli begins to pass out of the patient's airway and the capnogram measures a rapid increase in $CO_2$ as the expiratory phase of the ventilation cycle proceeds. The third phase of the ventilation cycle is known as the "alveolar plateau," during which a relatively constant $PCO_2$ is measured at the airway opening. The $PCO_2$ of the expired respiratory gas at the end of this third phase of the ventilation cycle ($PETCO_2$) is typically of particular interest as it represents the last alveolar gas sampled at the airway opening during expiration. Finally, the fourth phase of the ventilation cycle is the inspiratory downstroke, during which the next inspiratory phase begins.

While these direct capnographic measurements at the airway opening do provide the clinician with important diagnostic information, the usefulness of such information is limited due to the fact that direct capnographic measurements of this type merely measure the partial pressure of $CO_2$ without relating such measurement to the volume of respiratory gas that is passing through the airway opening as the measurement is taken. In view of this shortcoming of traditional capnography, it is now believed that a measurement of volume-normalized average alveolar $PCO_2$ and pulmonary carbon dioxide elimination ($\dot{V}_{CO_2}$) are more clinically useful than the traditionally used end-tidal $PCO_2$ ($PETCO_2$).

Additionally, anesthesiologists, pulmonologists and critical care physicians are now beginning to consider another measurable variable known as "pulmonary carbon dioxide elimination per breath ($\dot{V}_{CO_2,br}$)." $\dot{V}_{CO_2,br}$ is arrived at by multiplication and integration of the airway flow and $PCO_2$ of the respiratory gas over all four phases of the respiratory cycle.

Also, there is growing acceptance of a technique known as indirect calorimetry (e.g., the measurement and/or computation of $CO_2$ elimination and $O_2$ uptake) during anesthesia or mechanical ventilation for the rapid detection of various untoward states such as metabolic upset (e.g. onset of anaerobic metabolism) or pulmonary embolism.

The measurement of pulmonary carbon dioxide elimination ($\dot{V}_{CO_2}$), pulmonary oxygen uptake ($\dot{V}_{O_2}$) and other indirect calorimetric measurements are facilitated by sampling of mixed respiratory gas. Such sampling of mixed respiratory gas may be accomplished in several ways. One way is to attach a collection vessel such as a bag to the ventilation circuit to collect expired respiratory gas over a period of time. This collection technique is time consuming and of limited value because the collected mixture of respiratory gas is obtained from only one location in the ventilation circuit (e.g., from the expiratory flow conduit). Another technique for sampling mixed respiratory gas is through use of an in-line bymixer device. The bymixer devices of the prior art have been constructed to continually divert a portion of respiratory gas flowing through a conduit into a reservoir. Sanjo, Y., Ikeda, K., *A Small Bypass Mixing Chamber for Monitoring Metabolic Rate and Anesthetic Uptake*, J. Clin. Monit. 1987; 3: 235-243; Breen P. H., Serina E. R., *Bymixer Provides On-Line Calibration of Measurement of Volume Exhaled Per Breath*, Ann. Biomed. Eng. 1997; 25:164-171. However, such prior art bymixers were typically difficult to construct and thus somewhat expensive. Also, the gas collection reservoirs of such prior art bymixers were of constant volume and the gas diverting tubes were of constant dimensions and, thus, could not be rapidly adapted or adjusted to accommodate patients of varying size (e.g., small pediatric patients and large adult patients) or changes that may occur in a particular patient's ventilation parameters or clinical status. Finally, the gas collection reservoirs of the prior art bymixers were prone to collect condensed water vapor and respiratory debris and were difficult to clean.

Accordingly, there remains a need in the art for the development of a new bymixer device that is simple and economical to use and is adjustable or adaptable so as to be useable in patients of varying size (e.g., small pediatric patients and large adult patients) and to optimize the continuing measurements made during a given procedure as changes occur in the ventilation circuit and/or in a patient's ventilation parameters or clinical status.

SUMMARY OF THE INVENTION

The present invention provides a new bymixer device and method for obtaining fast-response, accurate measurements of mixed expired gas fractions in various types of ventilation circuits, including open (non-rebreathing) circuits, closed (rebreathing) circuits, circle (rebreathing with optional added fresh gas) circuits, etc. The bymixer is of a novel parallel design, which facilitates adjustable response, easy cleaning, and construction from standard airway circuit components. This bymixer may serve as a platform or enabling technology to facilitate further use of indirect calorimetry during anesthesia and/or mechanical ventilation in critical care settings.

In accordance with the present invention, there is provided a bymixer device that is connectable to a respiratory gas flow conduit in a ventilation circuit (e.g., an open circuit, a closed circuit, a circle circuit, etc.) that is used for ventilating a human or veterinary patient. In general, the bymixer device of the present invention comprises a) a flow dividing manifold (e.g., a Y or T) for dividing the flow of respiratory gas into first and second flow streams, b) a main or direct flow channel that is connectable to the flow dividing manifold such that the first flow stream flows through the main flow channel, and c) a bypass flow channel that is connectable to the flow dividing manifold such that the second flow stream flows through the bypass flow channel. The bypass flow channel includes a flow-restrictor (e.g., an orifice or other flow-restricting structure) that partially blocks the flow of respiratory gas through the bypass flow channel, a mixing chamber positioned upstream of the flow restrictor and a sampling apparatus (e.g., a port for withdrawing samples of gas from said mixing chamber and/or sensor(s) positioned within the mixing chamber).

Further in accordance with the present invention, all or a portion of the bymixer device (e.g., the mixing chamber) may be automatically or manually adjustable or variable in size such that the volume of respiratory gas contained in the mixing chamber may be varied. In combination with, or separately from, such adjustability in the size of the mixing chamber, the degree of flow restriction caused by the flow restrictor may also be automatically or manually variable. The adjustability in mixing chamber size and/or degree of flow restriction allows the bymixer device to be adjusted or adapted in a manner that optimizes the rate of response in measurements made on mixed gas samples from the mixing chamber versus the homogeneity of the mixed gas samples obtained from the mixing chamber. Also, such adjustability of mixing chamber volume and/or flow rate through the mixing chamber allows the operator to adjust the bymixer to accommodate patients of varying size and/or to maintain optimal mixing of respiratory gas and monitoring of variables even when changes occur in the ventilation circuit or in a given patient's ventilation parameters and/or clinical status.

Still further in accordance with the present invention, one or more flow-disrupting surfaces and/or one or more mixing apparatus (e.g., mixing vanes, a rotating impeller, vibrating surface, moving member, etc.) may optionally be positioned in the mixing chamber to further enhance the mixing of respiratory gasses within the mixing chamber.

Still further in accordance with the present invention, there is provided a bymixer device that comprises an inflow port; a main flow channel; a mixing chamber; and an outflow port. Such bymixer device is constructed such that i) most of the gas which enters the inflow port will pass into the main channel; ii) a portion of the gas which enters the inflow port will pass into the mixing chamber, iii) gasses that exit the main flow channel and mixing chamber will subsequently flow out of the outflow port and iv) gasses from a plurality of consecutive breaths will become mixed within the mixing chamber. In at least some embodiments, least one of a) mixing chamber volume and b) mixing chamber flow is/are adjustable.

Still further in accordance with the present invention, there is provided a bymixer device comprising a) a shell having a hollow mixing chamber cavity therewithin; b) a tube extending through the hollow mixing chamber cavity, said tube having a lumen that defines a main flow channel, an inlet end of the tube being connectable to the respiratory conduit such that gas from the respiratory flow conduit flows into the inlet end of the tube and an outlet end of the tube being connectable to the respiratory conduit such that gas from the outlet end of the tube flows into the respiratory flow conduit; c) at least one opening near the inflow end of the tube through which a portion of the gas flowing through the main flow channel will pass into the mixing chamber; and d) at least one opening near the outflow end of the tube through which gas will pass from the mixing chamber back into the main flow channel. Optionally, in some embodiments of this device, the mixing chamber volume and/or mixing chamber flow may be adjustable.

Still further in accordance with the present invention, there is provided a bymixer device comprising a) a first tube member having an inflow end, an outflow end and a lumen which defines a main flow channel; b) a second tube member having an inflow end, an outflow end and a lumen which defines a mixing chamber; c) an inflow end cap member connected to the inflow ends of the first and second tube members and connectable to a first location on the respiratory gas flow conduit and d) an outflow end cap member connected to the outflow ends of the first and second tube members and connectable to a second location on the respiratory gas flow conduit. Such device is configured such that most of the gas that enters the inflow end cap member subsequently flows into the main flow channel, a fraction of the gas that enters the inflow end cap member subsequently flows into the mixing chamber and gas that exits the main flow channel and mixing chamber becomes recombined and delivered back into the respiratory gas flow conduit by the outflow end cap member. The fraction of gas that enters the mixing chamber may be fixed or variable. In some embodiments where the fraction of gas that enters the mixing chamber is variable, such variability may be provided by a plurality of interchangeable inserts that are insertable into the device to vary the relative amounts of the gas that pass into the main flow channel and mixing chamber. The volume of the mixing chamber may also be adjustable by inflating a bladder in the mixing chamber or inserting volume-occupying inserts into the mixing chamber.

Still further in accordance with the present invention, there are provided methods for using any of the bymixer devices of the present invention for obtaining mixed gas samples or measurements by sampling or measuring gas contained in the mixing chamber of the device.

Further aspects of the present invention will become apparent to those of skill in the art upon reading and understanding the following detailed description and examples.

BRIEF DESCRIPTION OF THE DRAWINGS

FIG. 2C is a longitudinal sectional view of a bymixer device of the present invention.

FIGS. 4A and 4B are graphs depicting data generated by Bland-Altman analysis. FIG. 4A shows the difference between the bymixer $P_{CO_2}$ and the value measured in the mixed collection of expired gas (exhaust gas collection bag) plotted against the average of the two values. FIG. 4B shows the ratio of the bymixer $P_{CO_2}$-to-gas collection $P_{CO_2}$ plotted against the average of the two values. (Dotted lines denote the mean±1.96 standard deviations (SD), which encompass 95% of the measurement sequences.) Each plotted point represents a steady state ventilation sequence of a $CO_2$-producing lung simulator, over a range of tidal volume (300-1200 ml) and respiratory frequency (6-20 breath/min). Measurements for mixing chamber volumes of 100, 150, and 200 ml are combined.)

FIG. 6C' is a cut-away view of segment 6C of FIG. 6A incorporating an optional seal member which forms a sliding seal between the walls of the first and second portions of the device.

FIG. 6C" is a cut-away view of segment 6C of FIG. 6A incorporating an optional rolling hinge which forms a seal between the walls of the first and second portions of the device.

FIG. 6C''' is a cut-away view of segment 6C of FIG. 6A incorporating optional threads and grooves on opposing surfaces of the walls of the first and second portions of the device such that one portion of the device may be rotatably advanced and retracted relative to the other.

FIG. 6D' is a partial view of the device of FIG. 6D showing the alignment of gas flow apertures that corresponds to the setting shown in FIG. 6D.

FIG. 6E' is a partial view of the device of FIG. 6E showing the alignment of gas flow apertures corresponding to the flowrate adjustor setting shown in FIG. 6E.

FIG. 6F' is a partial view of the device of FIG. 6F showing the alignment of gas flow apertures corresponding to the flowrate adjustor setting shown in FIG. 6F.

DETAILED DESCRIPTION

The following detailed description, and the accompanying drawings to which it refers, are provided for the purpose of describing and illustrating certain examples or specific embodiments of the invention only and not for the purpose of exhaustively describing all possible embodiments and examples of the invention. Thus, this detailed description does not in any way limit the scope of the inventions claimed in this patent application or in any patent(s) issuing from this or any related application.

Figure 1:
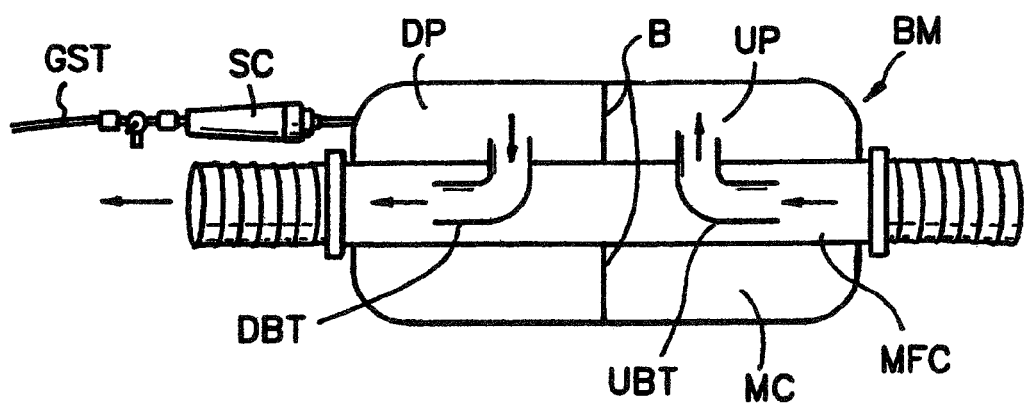
FIG. 1 is a schematic showing of a bymixer device of the prior art.

As shown in FIG. 1, a typical bymixer device of the prior art comprised a main flow conduit MFC that extends through a sealed mixing chamber MC. A right-angled upstream bypass tube UBT and a right-angled downstream bypass tube DBT extend through openings formed at longitudinally spaced-apart locations in the wall of the main flow conduit MFC, as shown. A porous baffle B divides the mixing chamber MC into an upstream portion UP and a downstream portion DP. A fraction of the respiratory gas flowing through the main flow conduit MFC would enter the upstream bypass tube UBT and would flow therethrough and into the upstream portion UP of the mixing chamber MC. Samples of mixed respiratory gas could be withdrawn from the downstream portion DP of the mixing chamber MC into the sample chamber SC where further mixing would occur and then through the gas sampling tube GST to the desired test apparatus where the desired analysis or measurement would be conducted. Mixed gas would also continually flow from the downstream portion DP of the mixing chamber MC, through the downstream bypass tube DBT and back into the main flow conduit MFC, thereby providing continual turnover of respiratory gas within the mixing chamber MC. This prior art bymixer has several limitations. For example, the size of the mixing chamber was fixed. Thus, the volume of gas within the mixing chamber could not be varied to optimize mixing of the respiratory gas or to respond to variations in patient size, physiology or clinical status. Similarly, the size and dimensions of the bypass tubes BP were fixed and could not be adjusted to vary the fraction of main flow into the mixing chamber MC. Also, the diameter of the upstream bypass tube was smaller than the diameter of the main flow conduit MFC and its position within the main flow conduit MFC was fixed. Thus, the sampling of gas was always obtained from the same region (e.g., the center) of the main flow conduit and in situations where flow though the main flow conduit is laminar, certain fractions of such laminar flow (e.g., that flowing though the periphery of the conduit) could flow past the upstream bypass tube UBT and would not be included in the sample shunted into the mixing chamber MC.

In clinical practice, there is substantial variation in the body size, respiratory physiology and clinical status of patients. Even during the course of a single procedure (e.g., a surgical procedure wherein the patient is connected to an anesthesia/ventilation circuit) there may be variations in the patient's respiratory physiology and/or clinical status. However, because the prior art bymixer (FIG. 1) had a mixing chamber MC of fixed size, it was not possible to adjust the size and/or volumetric capacity of the mixing chamber in response to such variations. Also, during manufacture, the positioning and securing of the upstream and downstream bypass tubes UBT, DBT was laborious and time consuming and the existence of these bypass tubes protruding into the lumen of the main flow conduit could, theoretically at least, result in trapping of condensed water vapor, microbes, mucoid matter or other contaminants.

Figure 2A:
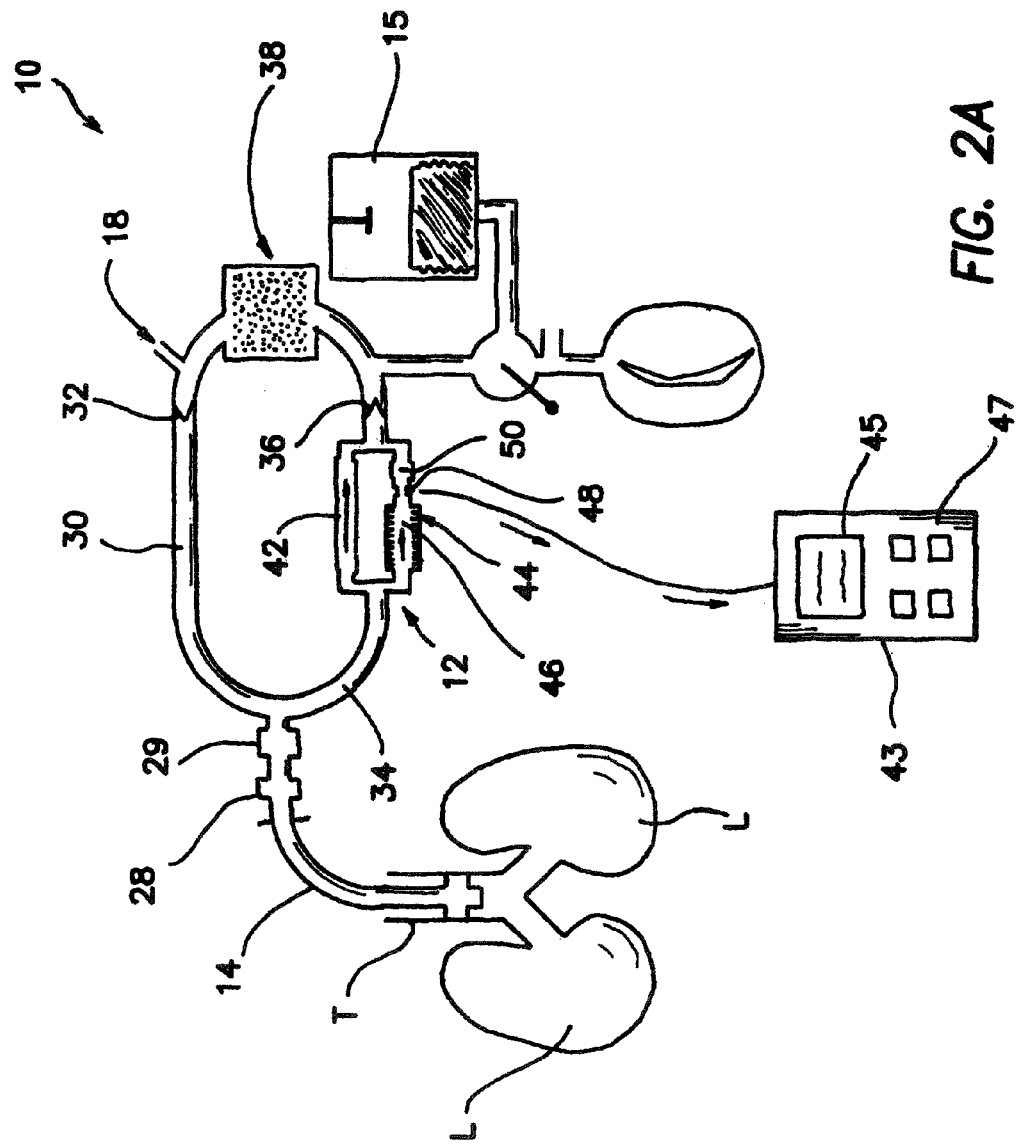
FIG. 2A is a schematic diagram of a circle-type ventilation circuit incorporating a bymixer device of the present invention.
Figure 2B:
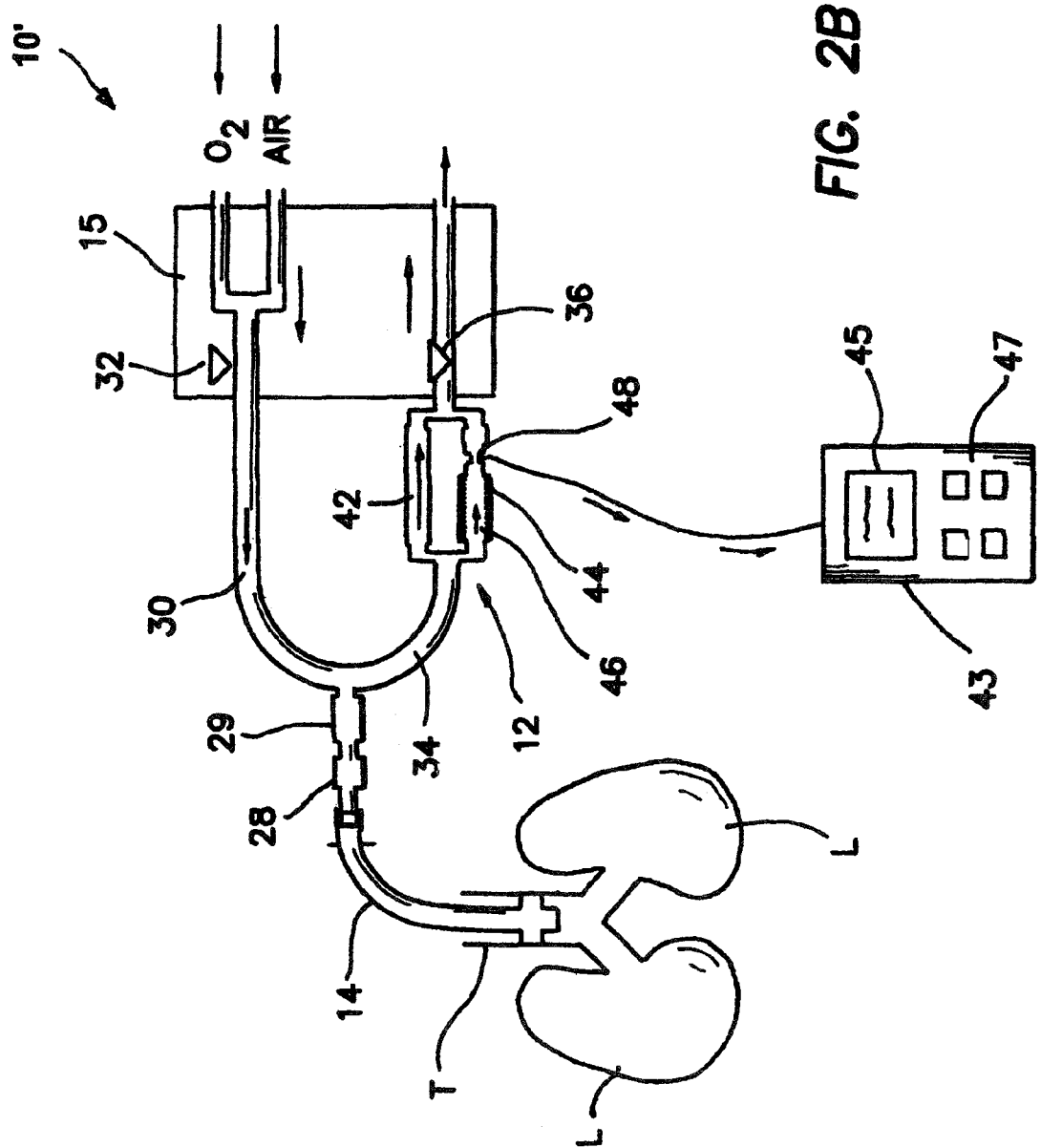
FIG. 2B is a schematic diagram of an open ventilation circuit incorporating a bymixer device of the present invention.

The bymixer device 12 of the present invention, as shown in FIGS. 2A, 2B and 2C, overcomes some or all of the shortcomings of the prior art bymixer. As explained herebelow, this new bymixer 12 is relatively simple and inexpensive to manufacture, relatively devoid of in-line obstructions and may optionally be adjustable in ways that allow the mixing chamber volume and/or the rate of flow through the mixing chamber to be modified or adjusted, thereby accommodating patients of varying body size, as well as differing or changing respiratory physiology and/or clinical status. Two types of ventilation circuits incorporating the bymixer 12 (a rebreathing circle circuit 10 and a non-rebreathing open circuit 10') are shown in FIGS. 2A and 2B, while details of the bymixer device 12 itself are shown in FIG. 2C.

Specifically, FIG. 2A shows an example of a circle ventilation circuit 10 which incorporates a bymixer 12 of the present invention. As shown, an airway device 14 such as an endotrachaeal tube, nasotracheal tube, tracheostomy tube, laryngeal mask airway or face mask is connected to the circle circuit 10 such that respiratory gas will flow into and out of the patient's lungs L. The circle circuit 10 comprises an inspiratory flow conduit 30 having a one-way inhalation valve 32 and an expiratory flow conduit 34 having a one-way exhalation valve 36, as shown, to alternately allow inspiratory inflow and expiratory outflow into and out of the patient's lungs L. During inspiration, inspiratory respiratory gas flows through inhalation valve 32, through inspiratory flow conduit 30, through the breathing device 14 and into the patient's lungs L. Thereafter, during expiration, respiratory gas is expelled from the patient's lungs L, though the airway device 14, though exhalation valve 36 and though the expiratory flow conduit 34. A pneumatochometer 29 and humidity/temperature sensor 28 are mounted near the airway device 14 to monitor respiratory rate, gas flow, humidity and temperature. The humidity/temperature sensor 28 may be any suitable type of humidity sensor, such as that described in U.S. Pat. No. 6,014,890 (Breen) entitled Fast Response Humidity and Temperature Sensor Device, the entirety of which is expressly incorporated herein by reference. In the example shown in FIG. 2A, the bymixer 12 of the present invention is attached to the expiratory flow conduit 34 such that expiratory respiratory gas flowing though the conduit 34 will enter a flow dividing manifold 40 (e.g., a Y or T) which channels a portion of that flow into a main flow channel 42 and a portion of that flow into a bypass channel 44.

As may be seen clearly in the enlarged sectional view of FIG. 2C, the bypass channel 44 comprises a mixing chamber 46, a flow restrictor 50 (e.g., an orifice) positioned downstream of the mixing chamber 46 and a sampling port 48 for withdrawing samples of mixed gas from the mixing chamber 46. It will be appreciated, however, that sampling of gas within the mixing chamber 46 may alternatively be accomplished without the need for withdrawal of gas through a sampling port by positioning one or more sensors (e.g., electrodes, optical sensors, chemical sensors, etc.) within the interior of the mixing chamber so that sample measurements may be made within the mixing chamber 46. Respiratory gas that has passed though the main flow channel 42 and bypass channel 46 then enters a flow combining manifold 54 (e.g., another Y or T) where it is recombined and continues through the downstream portion of the expiratory flow conduit 34.

In some embodiments of the invention, a monitoring device 43 may be connected to the sampling port 48 by a sampling tube 41 such that continuous or periodic samples of mixed gas may be withdrawn from the sample port 48 into the monitoring device 43. The monitoring device 43 may be operative to analyze, measure and/or otherwise determine any desired variables, such as volume-averaged alveolar $PCO_2$ ($P\overline{AE}_{CO_2}$); pulmonary carbon dioxide elimination ($\dot{V}_{CO_2}$); pulmonary oxygen uptake ($\dot{V}_{O_2}$); pulmonary carbon dioxide elimination per breath ($V_{CO_2,br}$); pulmonary oxygen uptake per breath ($V_{O_2,br}$); concentration or partial pressure of volatile gases; concentration or partial pressure of non-volatile gasses and/or other variables. In some instances, the monitoring device may incorporate a computer, microprocessor or other calculating apparatus and may be programmed or otherwise adapted to calculate one or more calculated values of interest based on one or more of the measured variables. In some instances, additional data such as patient body weight, barometric pressure, airway opening gas humidity and temperature, airway opening gas flow etc. may be input into the monitoring device 43, either by manual input (e.g., via a keyboard) or may be communicated by hard wired or wireless connection between the monitoring device 43 and one or more sensing apparatus operative to measure such values. These additional data (when obtained) may also be used in calculating some calculated values of interest. Examples of calculated values that may optionally be provided by the monitoring device include but are not limited to: pulmonary carbon dioxide elimination ($\dot{V}_{CO_2}$), pulmonary carbon dioxide elimination per breath ($V_{CO_2,br}$), pulmonary oxygen uptake ($\dot{V}_{O_2}$), pulmonary oxygen uptake per breath ($VO_{2,br}$), minute ventilation ($\dot{V}_E$), tidal volume ($V_T$), Vital Capacity (VC), etc. The monitoring device 43 may include, or may be connected to, a display for displaying the measured variables and/or or computed values. For example, a waveform display 45 may provide a display of one or more waveforms such as flow, pressure, capnography, oxygen concentration, spirometry, etc. Alternatively or additionally, one or more alphanumeric displays 47 (e.g., LED displays) may display numerical values and/or letters that constitute or relate to the variables mentioned above (i.e., flow, pressure, capnography, oxygen concentration, spirometry, etc.) determined using the bymixer and/or others such as peak inspiratory pressure, end tidal $CO_2$, expired $O_2$, inspired $O_2$, $CO_2$ elimination, $\dot{V}_{CO_2}$, and $O_2$ uptake, $\dot{V}_{O_2}$, tidal volume, minute volume, airway pressure, airway compliance, estimated energy required (EER), respiratory quotient (RQ), etc. In particular, the Respiratory Quotient (RQ) is a determined parameter calculated from the quotient of pulmonary carbon dioxide elimination ($\dot{V}_{CO_2}$) and pulmonary oxygen uptake ($\dot{V}_{O_2}$). The Respiratory Quotient is a very sensitive indicator of the metabolic state of the patient, particularly in its ability to detect the change from aerobic to anaerobic metabolism. The Respiratory Quotient depends only upon inspired and mixed expired gas fraction measurements for its calculation, and in particular, does not require any flow measurements. Thus, with a bymixer 12 on the expiratory flow conduit 34 (e.g., expired air limb of the ventilation circuit) and possibly, as necessary, another bymixer 12 on the inspiratory flow conduit 30 (e.g., the inspiratory limb of the ventilation circuit), the Respiratory Quotient can be measured and determined without the need for any flow measuring device.

One example of a monitoring device 43 that may be used is the Capnomac Ultima available commercially from Datex Medical Instruments, Instrumentarium Corp., Helsinki, Finland. Another example is the Datex-Ohmeda Division, Instrumentarium Corp. (Helsinki, Finland; Madison, Wis.) Airway Module, M-CAiOVX (gas composition/indirect calorimetry) and S/5 portable compact monitor, which can measure airway oxygen uptake and carbon dioxide elimination. The bymixer apparatus 12 can provide accurate, on-line and simultaneous measurements of $\dot{V}_{CO_2}$ and $\dot{V}_{O_2}$ to provide calibration values for the M-CAiOVX measurements. In at least some applications it may be of value to have a bymixer 12 of the present invention in a ventilation circuit in addition to another device for breath-by-breath calorimetric measurements at the patient's airway, such as the Datex-Ohmeda Airway Module, M-CAiOVX (gas composition/indirect calorimetry) and S/5 portable compact monitor. In this regard, the simultaneous side stream analysis/measurement of gas fractions at the airway opening, along with a measurement of flow at the airway opening (such as with a pneumotachometer) will allow the generation of breath-by-breath measurements of $VO_2$, $V_{O_2,BR}$ and $VCO_2$, and will allow the determination of $\dot{V}_{CO_2}$,br and $\dot{V}_{O_2,br}$ via the online multiplication and integration on these gas fraction and flow values measured at the airway opening. The bymixer flow measurement of $\dot{V}_{O_2}$ during steady state can be used to calibrate these more unstable breath-by-breath measurements of indirect calorimetry. Then, during non-steady state conditions, where the bymixer flow measurement may not react fast enough to changes in patient pathophysiology, the breath-by-breath measurements maybe used to follow the patent's condition.

In some embodiments, the system may be fully or partially automated. For example, the system may include a programmable controller (e.g., a microprocessor or computer) that may receive input signal(s) from the monitoring device 43 and, in response to predetermined changes in measured variables or calculated values, may issue control signals to certain components of the system that are equipped to undergo changes in response to such automated control signals. For example, such automated control system may optimize the size of the mixing chamber 46 and/or the diameter of the flow restricting orifice 50. In some applications, it may suggest or facilitate changes in ventilator settings, such as $F_{I_{O_2}}$, respiratory rate, tidal volume, and positive end expiratory pressure (PEEP), to remedy undesirable changes or trends in measured variables or computed values.

Also, in some embodiments, the monitoring device 43 may also include one or more auditory or visual alarms that will be triggered when certain measured variables and/or computed values move outside of preset limits.

In the circle ventilation circuit 10 shown in FIG. 2A, the portion of the expiratory flow conduit downstream of the bymixer 12 flows into a $CO_2$ absorber 38 (e.g., SODA-SORB® 4-8 IND N MED, Daerx® Container Products, Cambridge, Mass. or ThermHOAbsorb™, Raincoat Industries, Inc., Louisville, Ky.) which removes $CO_2$ After exiting the $CO_2$ absorber 38, the expiratory flow (less $CO_2$ absorbed by the absorber 38) may be mixed with fresh gas (e.g., air and/or oxygen and/or nitrogen and/or anesthetic gas(es)) entering through fresh gas inlet 18, and flows through the inspiratory flow conduit 30 and back into the patient's lungs L as described above. This circle (rebreathing) ventilation circuit 10 may be used in various settings including during anesthesia where it is desired to recycle volatile or gaseous anesthetics and in certain other types of mechanical ventilation (including anesthesia) where it is desirable to prevent loss of the temperature and humidity of the expired respiratory gas and/ or where it is undesirable to allow the expired respiratory gas to escape into the surrounding room air.

The open ventilation circuit 10' shown schematically in FIG. 2B includes many of the same components as the circle circuit 10 of FIG. 2A. However, in this open circuit 10', the expired respiratory gas is allowed to vent out of the circuit 10', downstream of the bymixer and only fresh respiratory gas enters the inspiratory flow conduit 30. This open (non-rebreathing) circuit 10' is typically used in mechanical ventilation of non-anesthetized critical care patients or during surgical procedures in which volatile or gaseous anesthetics are not used. Although FIGS. 2A and 2B show ventilation circuits 10, 10' in which the bymixer 12 is located on the expiratory flow conduit 34, it will be appreciated that the bymixer 12 may also be located on the inspiratory flow conduit 30 to obtain time-averaged or mixed samples of inspiratory respiratory gases.

Optionally, in some embodiments of the invention, the mixing chamber 46 is of variable size. This may be accomplished by constructing the mixing chamber of common corrugated tubing or other expandable or telescoping tubing such that the size and/or internal volume of the mixing chamber 46 may be varied. The advantages and clinical utility of this aspect of the invention are described more fully herebelow where reference is made to certain experimental data showing the utility of this feature as shown in FIGS. 3A-5B.

Optionally, in some embodiments of the invention, the flow restricting orifice 50 may be of variable size or diameter to permit the operator to easily adjust the flow rate of gas through the mixing chamber to optimize mixing.

Validation and Testing of Bymixer
Theoretical Background

Measurement of mixed expired gas concentrations is an essential component of the methodology to measure $CO_2$ elimination ($\dot{V}_{CO_2}$) and pulmonary oxygen uptake ($\dot{V}_{O_2}$) at the airway opening. In the normal condition where $CO_2$ is absent from inspired gas, $\dot{V}_{CO_2}$ is given by $$\dot{V}_{CO_2} = \dot{V}_E F\bar{E}_{CO_2} \qquad \text{(Eq. 1)}$$

where $\dot{V}_E$ is the expired ventilation and $F\bar{E}_{CO_2}$ is the mixed expired $CO_2$ fraction.

On the other hand, $\dot{V}_{O_2}$ is the difference between inspired and expired $O_2$ volumes, as given by $$\dot{V}_{O_2} = \dot{V}_I \cdot F_{O_2} - \dot{V}_E \cdot F\bar{E}_{O_2} \qquad \text{(Eq. 2)}$$

where I denotes inspiration. Because expired volume is increased by increased temperature (T) and added water vapor (increased humidity), volumes must be corrected to standard temperature and pressure, dry (STPD) conditions or the error in $\dot{V}_{O_2}$ can approach 50% as $F_{I_{O_2}}$ increases to unity. Because accurate differences between $\dot{V}_I$ and $\dot{V}_E$ are difficult to measure, the Haldane transformation is usually used, invoking conservation of the inert gas, nitrogen ($\dot{V}_I \cdot F_{I_{N_2}} = \dot{V}_E \cdot F_{E_{N_2}}$). By substitution into Eq. 2, $V_{O_2}$ can be expressed as a function of only $\dot{V}_E$, where:

$$\dot{V}_{O_2} = \dot{V}_E \cdot (F_{I_{O_2}} \cdot F_{E_{N_2}}/F_{I_{N_2}} - F_{E_{O_2}}). \quad \text{(Eq. 3)}$$

Regardless of whether T and humidity differences between inspiration and expiration are managed by the Haldane transformation (Eq. 3) or by separate measurements of airway T and relative humidity (RH) (Eq. 2), the determination of $\dot{V}_{CO_2}$ and $\dot{V}_{O_2}$ requires measurements of mixed expired and inspired gas fractions. The classic method to obtain mixed expired gas fractions is to collect exhaled gas over a number of breaths in a collection chamber connected to the expiratory outlet of the ventilator. However, expired gas collection cannot be conducted in the anesthesia semi-open or closed anesthesia circle ventilating circuit because expired gas passes through a $CO_2$ absorber to become the next inspiration. Instead, to measure mixed expired gas fractions in the circle circuit, Applicant and other workers have used an inline bypass mixing chamber (e.g., a bymixer as shown in FIG. 1). The term "bymixer" is named for the by-pass of a constant fraction of total flow through a mix-ing chamber. However, the response time of that bymixer is long and fixed, the mixing chamber is difficult to fabricate, clean and sterilize, and the device is bulky.

To solve these problems, the bymixer 12 of the present invention may be constructed from common anesthesia circuit components (FIG. 2C). Instead of diverting gas flow into a separate, large mixing chamber, the new clinical bymixer incorporates a novel parallel tubing design. A constant fraction of total $\dot{V}$ is diverted through the mixing chamber 46 (e.g., corrugated collapsible/expandable pediatric anesthesia circuit tubing), whose volume can be adjusted (e.g., by collapsing or expanding the corrugated tubing). The resistor 50 controls the fraction of bypass $\dot{V}$ to total flow. As gas passes through the mixing chamber 46, it mixes longitudinally in the tubing. Flow-averaged mixed gas is sampled at the sampling port 48 for analysis by a side-stream sampling monitor 43.

In this study, the following questions were tested and answered: Is a constant fraction of main gas flow diverted through the mixing chamber (mandatory for mixed bypass gas samples to accurately represent total gas flow)? Does the longitudinal design of the tubular mixing chamber provide adequate mixing (no significant breath-to-breath variation of mixed gas fractions)? What is the fastest but still accurate response of the new clinical bymixer when the mixing chamber volume is decreased (shortest length of mixing tubing)? Does continuous side-stream sampling flow rate affect the measurement of mixed gas fraction?

In order to test the performance of the new bymixer 12 during cyclical changes in gas fractions under actual expiratory flow conditions, the bymixer 12 was interposed in the expiratory flow conduit 34 of a ventilation circuit that was attached to a $CO_2$-producing metabolic lung simulator as described in U.S. Provisional Patent Application Ser. No. 60/417,982, which is expressly incorporated herein by reference and in Rosenbaum, A, and Breen, P. H., *Novel, Adjustable, Fast Response Bymixer Measures Mixed Expired Gas Concentrations In Circle Circuit*, Anesth Analg; 97: pp. (2003). Measurement of bymixer mixed expired $P_{CO_2}$ was compared to the value in a gas collection from the exhaust port of the open circuit ventilator. The use of the metabolic lung simulator was mandatory for the execution of this study, in order to provide a wide and controlled range of tidal volume, respiratory frequency (f), and mixed expired $P_{CO_2}$.

Methods

Design and Construction of the New Clinical Bymixer

The bymixer 12 divides incoming total gas flow into two parallel channels, a main flow channel 42 and a bypass flow channel 44. In the bymixer 12 used in this experiment, the main flow channel 42 was constructed of a 24 cm length of standard ¾ inch PVC pipe (22 mm ID). The mixing chamber 46 was a length of expandable/collapsible pediatric anesthesia circuit tubing (15 mm ID, Expandoflex, Cleveland Tubing Inc., Cleveland, Tenn.). This adjustable tubing was connected, in series, to the sampling port 48 which was constructed from a sampling port adapter available commercially from Datex-Engstrom Division, Instrumentarium Corp., Helsinki, Finland, a flow resistor 50, and a 12 cm length of standard ¾ inch PVC tubing. The flow resistor 50 was constructed by drilling a 4 mm diameter hole in a plastic cap (NAS-820-10, Niagra Plastics, Erie, Pa.), placed inside a connector (Multi Adapter, Hudson RCI, Temecula, Calif.; 15 mm ID, 22 mm OD). In this study, the adjustable tubing lengths were 50, 65.5, and 121 cm, which generated mixing chamber volumes (measured up to the sampling port) of 100, 150, and 200 ml, respectively. The volume of the bypass channel 44 from the sampling port 48 to the downstream "Y" connector 54 was 53 ml. The main flow channel 42 and bypass flow channel 44 were connected at each end by identical "Y" connectors 40, 54 (supplied with standard anesthesia circle circuits). Volumes of channel components were determined by water displacement.

Determination of Time Constant (Bymixer Response)

The anesthesia monitor (Capnomac Ultima, Datex Medical Instruments, Instrumentarium Corp., Helsinki, Finland) sampling line was connected to the bymixer sampling port (200 ml/min) and the pneumotachometer adapter was attached to the inlet of the bymixer. $F_{O_2}$ (paramagnetic) and bymixer total flow were continuously captured (100 Hz) by analog-to-digital (A/D) acquisition PC card (DAQcard 700, National instruments, Austin, Tex.) installed in a notebook computer (Inspiron 3800, Dell Computer Corp., Austin, Tex.). The digital data acquisition system was driven by a custom program (Delphi Pascal, Borland International, Scotts Valley, Calif.) written by our computer support specialist (David Chien) and one author (PHB). The bymixer was flushed with air to provide a baseline $F_{O_2}$ of 21%. At time zero, oxygen flow of either 4, 8, or 12 L/min was abruptly connected to the bymixer input. The time constant ($\tau$) was the time interval, from time zero, until $F_{O_2}$ increased to 63% of its maximal value. The time constant was corrected for the $F_{O_2}$ transport delay (2.95 sec) down the side-stream sampling system.

The bymixer response was also tested in the exhalation limb during mechanical ventilation of the $CO_2$-producing metabolic lung simulator. Steady state ventilation was established at minute ventilation of 4, 8, or 12 L/min (respiratory frequency, f, was 10/min and inspiration-to-expiration time ratio, I:E, was 1:2). The bymixer 12 (100 ml mixing chamber) was separately flushed with air. During the inspiratory phase, the bymixer 12 was abruptly interposed in the expiratory flow conduit 34 of the ventilation circuit (time zero). Because bymixer data during ventilation was periodic and available only during expiration, Applicant used the time for bymixer $P_{CO_2}$ (infra-red analysis) to reach 95% of its maximum value. This time for 95% response was corrected for the $P_{CO_2}$ transport delay (1.76 sec) down the side-stream sampling system.

Validation of the Accuracy of the New Clinical Bymixer

To test the bymixer 12, Applicant used a modification of the metabolic lung simulator bench setup. The commercial lung simulator (Dual Adult TTL, Model 1600, Michigan Instruments, Inc., Grand Rapids, Mich.) generated a physiologic ventilation waveform by combining airway resistance elements to a bellows (residual volume=920 ml), whose compliance can be adjusted by springs. The mechanical lung was connected by a circular circuit to a metabolic chamber (airtight 18.6 L pail). Carbon dioxide was continuously infused (200 ml/min) by calibrated rotameter into the metabolic chamber. A fan and a baffle system inside the chamber ensured a homogeneous gas mixture. An occlusion roller pump (15 mm ID tubing; Precision Blood Pump, COBE Perfusion system, Lakewood, Colo.) generated constant gas flow (5 L/min) between the metabolic chamber and the mechanical lung. The mechanical lung was ventilated with 30% oxygen (Servo Ventilator 900C, Siemens, Sweden). The bymixer 12 was interpolated in the expiratory limb of the open circuit (no rebreathing).

For each length of mixing chamber expandable tubing, the bymixer 12 was tested during different ventilatory patterns, encompassing combinations of tidal volume (300-1200 ml) and respiratory f (6-20 breath/min). I:E ratio was 1:2. Gas was continuously sampled from the bymixer by the side-stream capnometer (bymixer $P\bar{E}_{CO_2}$). Before measurements began at each ventilator setting, steady state was confirmed by stable values of $P_{ET_{DO_2}}$ and bymixer $P\bar{E}_{CO_2}$. A measurement sequence consisted of continuous digital acquisition of bymixer $P\bar{E}_{CO_2}$ and simultaneous collection of expired gas in a 15 L gas-impermeable collection bag (Hans Rudolph, Kansas City, Mo.) connected to the ventilator exhaust port. Measurements were conducted for 3 min (higher minute ventilation) to 5 min (lower minute ventilation). After the measurement sequence, the expired gas collection was mixed by shaking and agitating small balls inside the bag. Gas collection $P\bar{E}_{CO_2}$ was measured by attaching the side-stream sampling line to a stop-cock on the collection bag. Prior to each measurement sequence, the collection bag was emptied by vacuum to prevent gas dilution error. After attaining steady state and just before gas collection began, the dead space of the bag was flushed with exhaled gas from the ventilator exhaust port. Time-averaged bymixer $P\bar{E}_{CO_2}$ was compared to the value measured in the simultaneous expired gas collection.

Effect of Tidal Volume and Respiratory Frequency on Oscillations of Bymixer $P\bar{E}_{CO_2}$ Using the above Validation experimental setup and measurement sequences in the bymixer (150 ml mixing chamber volume), Applicant conducted two additional protocols which measured oscillations of bymixer $F\bar{E}_{CO_2}$. First, respiratory frequency was held constant (10 br/min) and tidal volume was varied from 300 to 1200 ml. Second, tidal volume was held constant (900 ml) and respiratory frequency was varied from 6 to 20 br/min.

Effect of Intermittent (Instead of Continuous) Sampling from the Bymixer Port

Applicant conducted an additional validation protocol using the bymixer 12 with its mixing chamber 46 volume set at 150 ml.). Gas was intermittently sampled from the bymixer sampling port 48, by manipulation of a 3-way stopcock, for short periods (about 3 sec). Several intermittent samples from the bymixer 12 were averaged for comparison with the expired gas collection (3-5 min), at each ventilator setting of tidal volume and frequency.

Data Analysis

Bymixer bypass flow ($\dot{V}_{BYPASS}$) was calculated by $$\dot{V}_{BYPASS} = V_{BYPASS}/\tau, \quad \text{Eq. 4}$$

where, $V_{BYPASS}$ was the volume of the mixing chamber (measured up to the sampling port), and $\tau$ was the measured time constant of the bymixer. Then, $$\text{Bymixer Bypass Ratio} = \dot{V}_{BYPASS}/\dot{V}_{TOTAL}, \quad \text{Eq. 5}$$

where $\dot{V}_{TOTAL}$ was the total gas flow entering the bymixer.

In the validation of average bymixer $P_{CO_2}$ versus the value measured in the expired gas collection (metabolic lung simulator), $$\text{bymixer } P\bar{E}_{CO_2} = (\int_{t_0}^{t_{end}} P_{CO_2}(t) \cdot dt)/(t_{end} - t_0), \quad \text{Eq. 6}$$

where dt is the digital sampling interval ($1/100$ Hz) and $t_0$ and $t_{end}$ were the beginning and end sampling times (sec) of bymixer $P_{CO_2}$.

Bymixer $P\bar{E}_{CO_2}$ were compared to expired gas collection $P\bar{E}_{CO_2}$ by least squares linear regression (slope, Y-intercept, and coefficient of determination, $R^2$) and by the limits of agreement technique described by Bland and Altman. Differences between groups were sought by t-test or by analysis of variance (ANOVA). Computer programs were used for data analysis (Excel spreadsheet, Microsoft Corp., Redmond, Wash.), statistical testing (SigmaStat, SPSS, Chicago, Ill.), and graphical presentation (SigmaPlot 8.0, SPSS).

Results

Figure 3A:
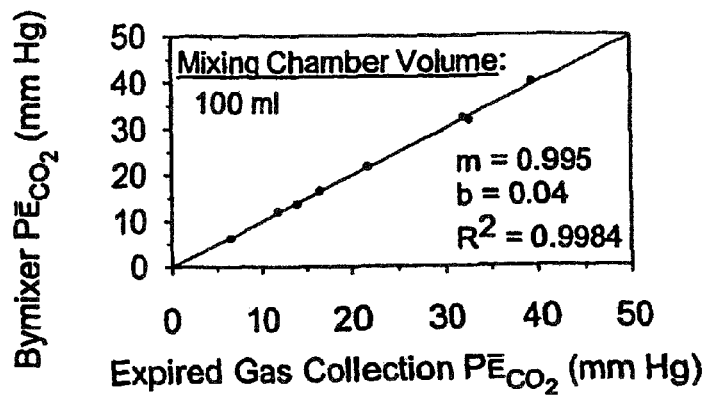
FIGS. 3A, 3B and 3C are graphs showing the correlation of bymixer mixed expired $P_{CO_2}$ ($PE_{CO_2}$) versus $PE_{CO_2}$ measured in a mixed collection of expired gas, for mixing chamber volumes of 100, 150, and 200 ml. Each plotted point represents a steady state ventilation sequence of a $CO_2$-producing lung simulator, over a range of tidal volume (300-1200 ml) and respiratory frequency (6-20 breath/min); m, slope; b, Y-intercept; and $R^2$, coefficient of determination (linear regression).
Figure 3B:
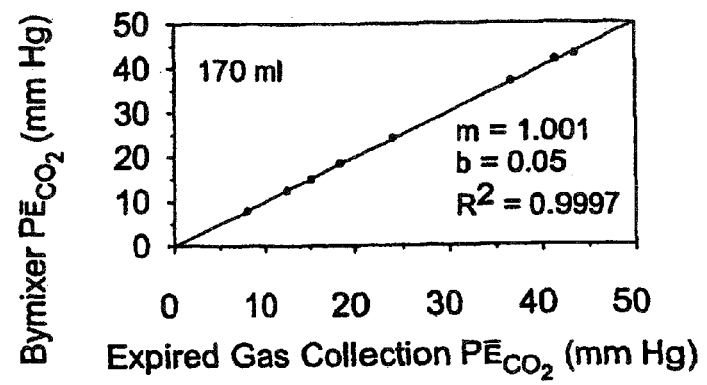
Figure 3C:
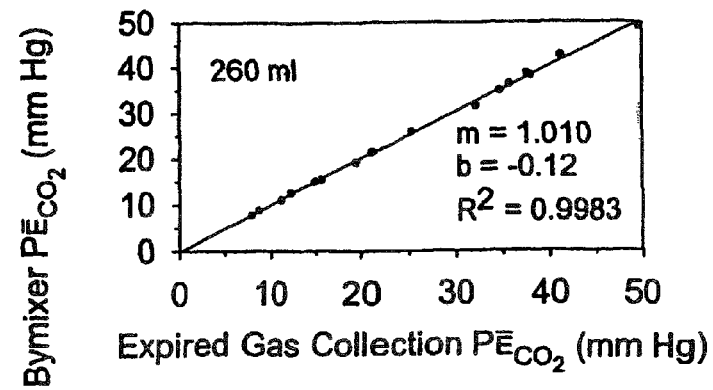

FIGS. 3A-C display the excellent linear regression correlation between bymixer $P\bar{E}_{CO_2}$ and the value measured in the expired gas collection over a wide range of $P\bar{E}_{CO_2}$ (6-50 mm Hg), for the bymixer with mixing chamber volumes set to 100, 150, and 200 ml. There was no significant difference in bymixer $P\bar{E}_{CO_2}$ accuracy among the mixing chamber volumes (ANOVA analysis of the $P\bar{E}_{CO_2}$ differences between the bymixer and expired gas collection measurements). For the bymixer set to mixing chamber volume of 150 ml, there was no significant difference in $P\bar{E}_{CO_2}$ accuracy between continuous and intermittent sampling from the bymixer port.

The Bland-Altman analysis derived the Limits of Agreement (LOA) as 0.07±0.93 mm Hg (FIG. 4A). Measurements for mixing chamber volumes of 100, 150, and 200 ml were combined. Inspection of the graph revealed that the $P_{CO_2}$ difference, between the bymixer measurement and the simultaneous value measured in the expired gas collection, increased as the measurement increased along the x-axis. To correct for this effect, FIG. 4B plotted the $P_{CO_2}$ ratio (bymixer/bag) versus the average of the two values. The calculation of LOA (1.00±0.03) demonstrated that 95% of the bymixer $P_{CO_2}$ measurements were within 3% of the expired gas collection value.

Figure 5A:
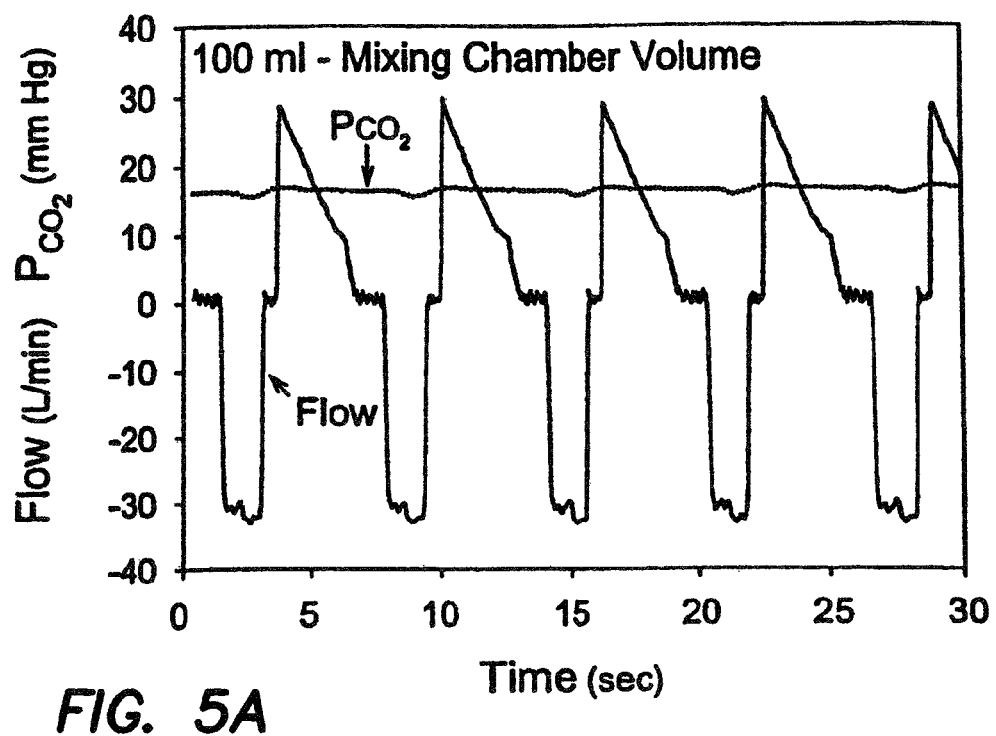
FIGS. 5A and 5B are graphs showing the effect of mixing chamber volume on bymixer $P_{CO_2}$ during continuous sampling from the bymixer port (200 ml/min) by the side-stream gas analyzer. Data were digitally acquired at 100 Hz. Airway opening flow was processed by moving average filter over 7 data points to remove signal noise. For clarity, every $20^{th}$ data point was plotted for bymixer $P_{CO_2}$. Relative to the flow signal, $P_{CO_2}$ was advanced in time by transport delay, the time to aspirate gas through the sampling line. Transport delay was measured previously in a bench setup. Respiratory frequency was 12 breath/min and tidal volume was 600 ml. With the mixing chamber volume of 100 ml (upper panel), oscillations in bymixer $P_{CO_2}$ were about 1.3 mm Hg. The larger mixing chamber of 200 ml (lower panel) generated only tiny oscillations in bymixer $P_{CO_2}$ of about 0.2 mm Hg.
Figure 5B:
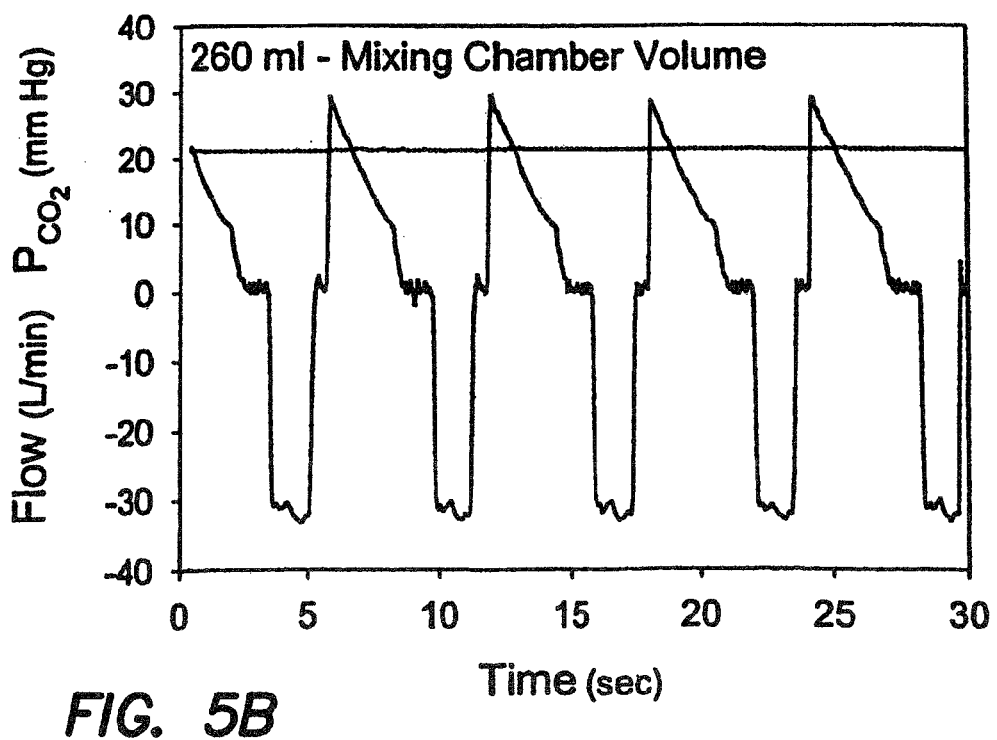

FIGS. 5A and 5B displays the breath-by-breath oscillations in $P_{CO_2}$ measured during continuous aspiration from the bymixer into the side-stream sampling gas analyzer. Oscillations in $P_{CO_2}$ were larger with the smaller bymixer mixing chamber volume. Table 1, below, displays that the average $P_{CO_2}$ oscillations increased from 0.1 to 0.7 mm Hg as bymixer mixing chamber volume decreased from 200 to 100 ml. The plot of $P_{CO_2}$ oscillation (mm Hg) versus $V_T$ (ml) (constant f) generated a significant direct relationship (slope=0.0016; Y-intercept=−0.69; $R^2$=0.92). The plot of $P_{CO_2}$ oscillation (mm Hg) versus f (min$^{-1}$) (constant $V_T$) resulted in a significant inverse relationship (slope=−0.062; Y-intercept=1.22; $R^2$=0.91). Thus, $P_{CO_2}$ oscillations increased in magnitude as $V_T$ increased and f decreased.

The ratio of bypass flow to total flow was similar (1:9) for the 3 mixing chamber volumes (Table 1). The time constant ($\tau$) of the bymixer response to a change in input gas concentration (at 8 L/min) ranged from 6.4 to 14.1 sec for the smallest (100 ml) to largest (200 ml) mixing chamber volumes. Tripling of the time constant predicts 95% response. During minute ventilation of the metabolic lung simulator at 4, 8, and 12 L/min, the times for 95% response of the bymixer (100 ml volume) were 19.0, 12.6, and 6.6 sec, respectively, significantly less than the values of $3\tau$ (Table 1).

Discussion

The bymixer 12 of the present invention incorporates a new design, compared to the classic bymixer. Instead of diverting a portion of main flow into a surrounding reservoir in the classic bymixer (e.g., the prior art bymixer shown in FIG. 1), the bymixer 12 of the present invention diverts a fraction of main flow through a parallel, longitudinal and adjustable mixing chamber 46. The flow resistor 50 (variable orifice) provided an easy control of fraction of bypass flow. To provide an accurate mixed average gas fraction of total flow, the ratio of bypass flow/total flow must remain constant and gas must adequately mix by the time it reaches the sampling port 48. FIGS. 3A, 3B and 3C demonstrate the excellent correlation of bymixer $P\bar{E}_{CO_2}$ compared to the simultaneous value measured in the expired gas collection, over a wide range of $V_T$, f, and $P_{CO_2}$. The Bland-Altman Limits of Agreement analysis shown in FIGS. 4A and 4B demonstrates excellent bymixer measurement accuracy, where 95% of the bymixer measurements were within 3% of the simultaneous value measured in the mixed expired gas collection. If present, the small bymixer $P_{CO_2}$ oscillations (FIG. 5 and Table 1) were time-averaged and did not degrade bymixer performance for mixing chamber volumes of 100, 150, and 200 ml.

The small bymixer $F_{CO_2}$ oscillations, when present, represented slight incomplete mixing in bypass flow. $F_{CO_2}$ oscillations decreased with smaller $V_T$ because the ratio of $V_T$-to-mixing chamber volume decreased. $F_{CO_2}$ oscillations decreased with higher f (at constant $V_T$) because increased overall gas flow (and velocity) improved gas mixing. The corrugations of the mixing chamber tubing presumably added to gas mixing. The presence of bymixer $P_{CO_2}$ oscillations was not significant, since simple time-averaging of the oscillations resulted in excellent bymixer accuracy (FIGS. 3A-C and 4A-B).

In summary, the novel, parallel design of the bymixer 12 provides accurate measurement of mixed expired gas fractions in the anesthesia circle circuit. Simple changes in mixing chamber volume allow adjustable bymixer response time. The fast bymixer response (time constant=6.4 sec) should permit measurements to be updated every 20 sec (where 95% response occurs by 3 time constants). The bymixer 12 of the present invention can be constructed from standard anesthesia circuit components, attaches easily to the anesthesia machine inspired outlet and expired inlet ports, is simple to clean and sterilize, and has no reservoir that can trap condensed water vapor from expired gas. This new bymixer 12 may facilitate more widespread use of indirect calorimetry ($\dot{V}_{O_2}$ and $\dot{V}_{CO_2}$) during anesthesia and the non-invasive detection of metabolic upset (e.g. onset of anaerobic metabolism) and critical events (e.g. onset of pulmonary embolism).

TABLE 1

Effect of mixing chamber volume (V) on selected parameters of the new clinical bymixer (see FIG. 2)

| Mixing Chamber V (ml) | $\tau$ (4 L/min) (sec) | $\tau$ (8 L/min) (sec) | $\tau$ (12 L/min) (sec) | Bypass Flow Ratio | $F_{CO_2}$ Oscillations (mmHg) | slope | Y-intercept | $R^2$ |
|---|---|---|---|---|---|---|---|---|
| 100 | 14.1 | 6.4 | 4.0 | 1:8.6 | 0.68 ± 0.89 | 0.995 | 0.04 | 0.9984 |
| 150 | 24.7 | 9.0 | 6.3 | 1:9.1 | 0.57 ± 0.66 | 1.001 | 0.05 | 0.9997 |
| 200 | 32.3 | 14.1 | 9.1 | 1:9.7 | 0.14 ± 0.28 | 1.010 | −0.12 | 0.9983 |

For these mixing chamber volumes, the ratio of bypass flow to total flow was similar (1:9) because the major impedance to gas flow was the flow resistor. Increased length of the large bore tubing that formed the mixing chamber 46 tubing did not materially add to bypass flow resistance. Thus, dynamic response of the bymixer 12 can be improved by decreasing the volume of the mixing chamber 46 (e.g., in this example, by decreasing the length of the tubing). The data shown in Table 1 suggests that bymixer dynamic response (at 8 L/min) could be improved, beyond (less than) the 9.3 sec time constant of the bymixer with 100 ml mixing chamber, by further decreasing the volume of the mixing chamber 46. However, at some point, time-averaging of increasing $F_{CO_2}$ oscillations would significantly depart from the flow-averaged value and degrade bymixer accuracy. Interestingly, compared with constant gas flows (Table 1), the bymixer 12 demonstrated much faster response during mechanical ventilation of the metabolic lung simulator, presumably because the periodic, peak expiratory flows enhanced gas mixing in the bymixer 12.

There was no difference in bymixer accuracy between continuous and intermittent aspiration at the sampling port. Accordingly, the down-stream volume (measured from the sampling port) of the bypass channel was sufficiently large so that side-stream sampling (200 ml/min) did not spuriously sample gas from the main flow outlet during inspiration (when gas flow through the bymixer was zero).

In these data, $\tau$ was the time constant of the bymixer response to a change in input oxygen concentration, measured during three constant flow rates of $O_2$. Bypass flow ratio=bypass flow/total flow. $F_{CO_2}$ oscillations were measured during continuous aspiration from the bymixer sampling port. Slope, Y-intercept, and $R^2$ (coefficient of determination) characterized the correlation of bymixer mixed expired $F_{CO_2}$ ($F\bar{E}_{CO_2}$) and the value measured in a simultaneous collection of expired gas (FIGS. 3A-3C), during ventilation of the $CO_2$-producing lung simulator.

Figure 6:
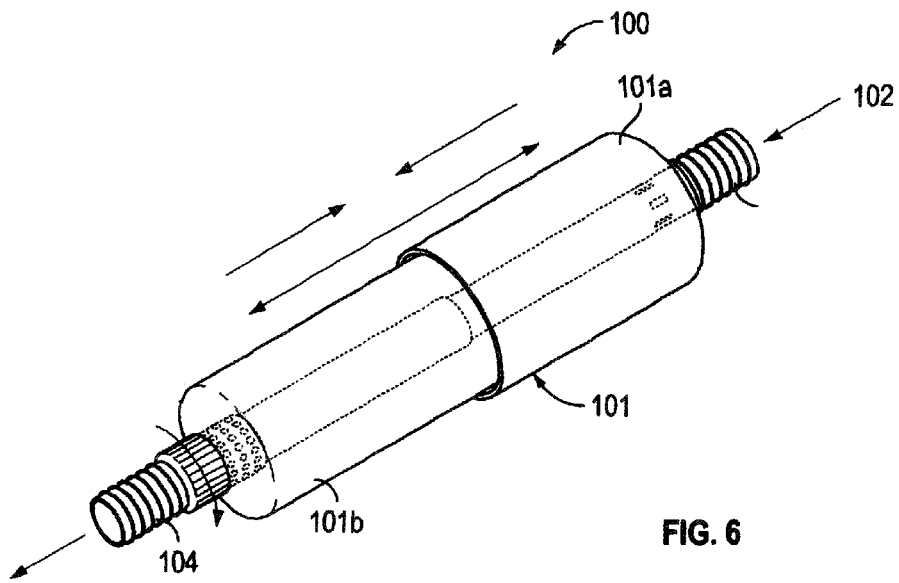
FIG. 6 is a perspective view of another embodiment of a bymixer device of the present invention.
Figure 6A:
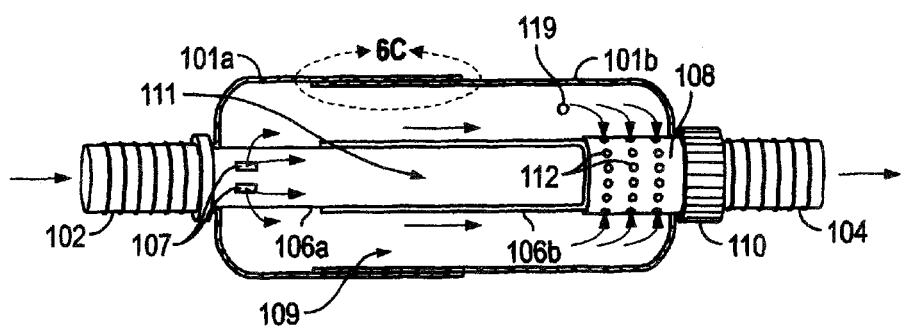
FIG. 6A is a partially-sectioned side view of the bymixer device of FIG. 6 with the mixing chamber of the device disposed in a short/low volume configuration.
Figure 6B:
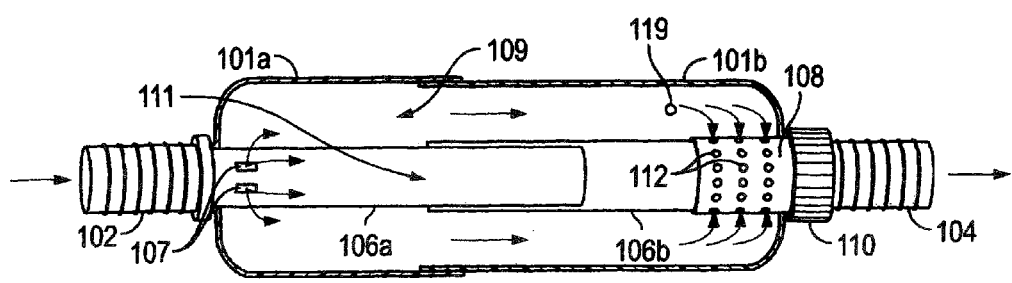
FIG. 6B is a partially-sectioned side view of the bymixer device of FIG. 6 with the mixing chamber of the device disposed in a long/high volume configuration.
Figure 6C:
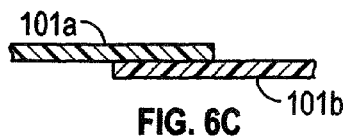
FIG. 6C is a cut-away view of segment 6C of FIG. 6A wherein the walls of the first and second portions of the device are in slidable abutting relationship.
Figure 6C:
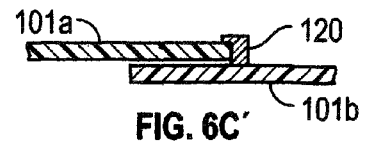
Figure 6C:
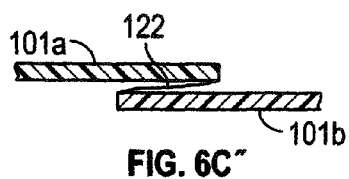
Figure 6C:
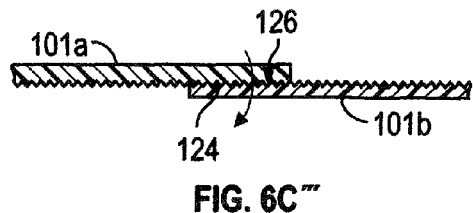
Figure 6D:
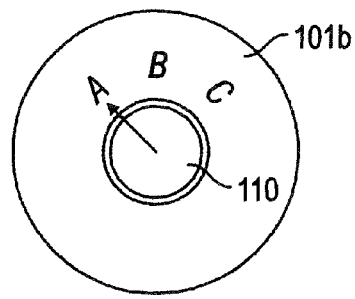
FIG. 6D is an end view of the downstream end of the device of FIG. 6B having an optional flowrate adjustor set in a first position.
Figure 6D:
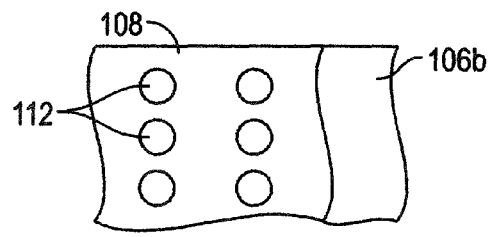
Figure 6E:
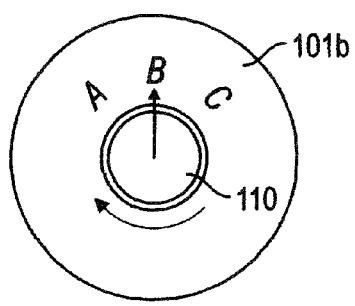
FIG. 6E is an end view of the downstream end of the device of FIG. 6B having an optional flowrate adjustor set in a second position.
Figure 6E:
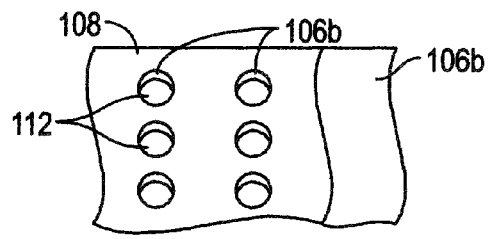
Figure 6F:
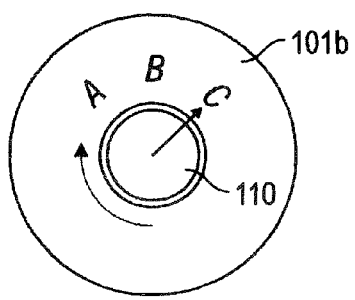
FIG. 6F is an end view of the downstream end of the device of FIG. 6B having an optional flowrate adjustor set in a third position.
Figure 6F:
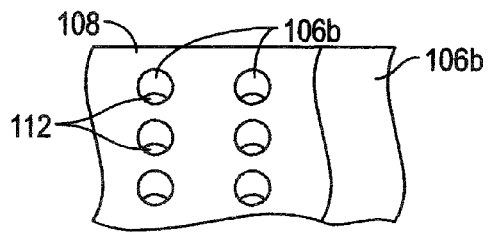

FIGS. 6 through 6F' show another embodiment of a bymixer device 100 of the present invention. This device 100 is constructed in two portions 101a, 101b to allow adjustment of the volume of the mixing chamber 109 by lengthening or shortening the device 100. Also, optionally, this device 100 may incorporate a flow rate adjustor 108 that allows a user to vary the flow rate of respiratory gas through the mixing chamber 109. This embodiment of the device 100 may be small, compact and easy to manufacture, such as by industry standard injection molding techniques.

FIG. 6A displays a partial cross-section of the bymixer device 100. Gas enters the inlet 102 of the bymixer device 100 as depicted by the arrow. Gas entering the inlet 102 then continues through the lumens of telescoping tubes 106a, 106b which, in combination, form a main flow channel 111 sized to carry most of the gas through the bymixer device 100. A portion of the gas that flows into the first telescoping tube 106a passes out of apertures 107 and into the mixing chamber 109. Such apertures 107 may be formed at spaced-apart locations circumferentially around the tube 106a. Optionally, a turbulator or other turbulence-inducing apparatus may be positioned on the inner wall of, or within the lumen of, the inlet 102 to ensure homogenous or at least non-laminar flow of respiratory gas components as they enter the main channel 111, upstream of the apertures 107 where the gas exits the main channel 111 and enters the mixing chamber 109. Also, optional scoops, baffles or other flow-directing members may be provided on the interior of tube 106a to deflect, direct or force a portion of the gas flow from the lumen of tube 106 through apertures 107. Respiratory gas that enters the mixing chamber 109 through apertures 107 then flows through the mixing chamber 109, though holes 112, and back into the main flow channel 111 at the downstream end of the bymixer device 100. This re-combined gas flow then exits the main channel 111 through the outlet 104 of the bymixer device 100.

In the non-limiting example shown, the mixing chamber 109 is formed by a housing or outer shell 101 comprising an upstream and downstream cylindrical shell member portions 101a and 101b, the ends of which are bonded or otherwise attached to or integrally formed with the walls of upstream and downstream telescoping tube members 106a, 106b, as shown. In this manner, the upstream shell member portion 101a and the upstream telescoping tube 106a combine to form an upstream portion of the device 100 while the downstream shell member portion 101b and downstream telescoping tube 106b combine to form a downstream portion of the device 100. A sampling port 119 may be provided in the downstream shell member portion 101b to allow sampling of mixed gas from the mixing chamber 109 in the manner described above. Alternatively, as described above, one or more sensor(s) may be positioned within the mixing chamber for continuous, periodic or occasional sensing of variables or components of the gas flowing through the mixing chamber 109.

The volume of the mixing chamber 109 can be controlled by moving the upstream and/or downstream portions of the device 100 in telescoping fashion to lengthen or shorten the device 100 with resultant variation in the volume of the mixing chamber 109. To prevent unwanted leakage, substantially gas tight seals may be formed between adjacent surfaces of the shell member portions 101a, 101b. Substantially gas tight seals may also be formed between adjacent surfaces of the telescoping tube members 106a, 106b where desired, but in many embodiments these may be less critical because a small amount of gas leakage between the main channel 111 and the mixing chamber 109 will not significantly affect the measurement of mixed gas concentrations and the pressure gradient between the main channel 111 and the mixing chamber 109 may be insufficient to drive a substantial gas flow leak. Where desired, such gas tight seals may be constructed in any suitable way that will allow the intended adjustability of the device 100. Non-limiting examples of ways in which substantially gas tight seals may be constructed are shown in FIGS. 6C though 6C'''.

In the example of FIG. 6C, the walls of the upstream and downstream cylindrical shell member portions 101a and 101b are in firmly abutting but slidable contact with one another, thereby allowing the device to be lengthened or shortened by simply sliding the upstream and/or downstream portions of the device 100 toward or away from each other, to vary the size of the mixing chamber 109 as desired with no substantial leakage of gas between the adjacent surfaces of the walls.

In the example of FIG. 6C' a seal member 120, such as a smooth lubricious silicone or elastomeric ring, is attached to the upstream cylindrical shell member portion 101a. This seal member 120 rides in abutting contact with the outer surface of the downstream cylindrical shell member portion 101b, as shown. In this manner, the adjacent surfaces of the upstream and downstream cylindrical shell member portions 101a and 101b need not be in tight abutment and may even be slightly spaced apart, as the seal member 120 prevents substantial leakage of gas.

In the example of FIG. 6C'', one end of a rolling seal member 122 is attached to the upstream cylindrical shell member portion 101a and the other end of the rolling seal member 122 is attached to the downstream cylindrical shell member portion 101b, as shown. The rolling seal member 122 may comprise a flat cylinder of flexible material, such as a membrane or sheet formed of flexible silicone or other polymeric material. As the upstream and/or downstream cylindrical shell member portions 101a and 101b is/are moved relative to one another, the rolling seal member 122 will evert/inevert as necessary while the opposite ends of the rolling seal member 122 remain connected to the shell member portions 101a, 101b. In this manner the rolling seal member 122 provides a substantially gas tight seal between the shell member portions 101a, 101b while still permitting adjustment of the mixing chamber volume.

In the example of FIG. 6C''', matching threads 124, 126 are formed on the adjacent surfaces of the upstream and downstream cylindrical shell member portions 101a and 101b. The volume of the mixing chamber 108 can be increased or decreased by rotating one of the upstream or downstream cylindrical shell member portions 101a, 101b in either a clockwise or counterclockwise direction relative to the other, like turning a nut over a bolt. In at least some embodiments, the main channel 111 may not require threads and can continue to seal by a simple slide, even though the telescoping tube members 106a and 106b may rotate along with their associated shell member portions 101a, 101b.

FIGS. 6D through 6F' show non-limiting examples of how the flow rate adjustor 108 may be used to vary the resistance to (and hence the rate of) gas flow through the mixing chamber 109. In the example shown, the flow rate adjustor 108 comprises a tube that is disposed around a portion of the downstream telescoping tube member 106b adjacent the outflow port 104. Corresponding apertures are also formed in the underlying portion of the downstream telescoping tube member 106b. A dial 110 may be attached to the flow rate adjustor 108 and such dial 110 may be used to rotate the flow rate adjustor 108 relative to the underlying downstream telescoping tube member 106b to vary the alignment of apertures 112 of the flow rate adjustor 108 with the corresponding apertures underlying downstream telescoping tube member 106b. The degree of alignment of the apertures 112 determines the amount of resistance to flow from the mixing chamber 109 into the main channel 111. Detents can be incorporated into the surfaces between the tubular flow rate adjustor 108 and the downstream telescoping tube member 106b to allow for measured incremental movement and positioning of the flow rate adjustor 108 and corresponding markings may be provided to facilitate positioning of the dial 110 in specific positions that correspond to specific flow rates. Specific examples of this are seen in FIGS. 6D through 6F'. In FIGS. 6D and 6D', the dial 110 is set in a first position (labeled as Position A) whereby the apertures 112 are fully aligned to provide for minimum resistance to outflow and maximum flow rate through the mixing chamber 109. In FIGS. 6E and 6E', the dial 110 is set in a second position (labeled as Position B) whereby the apertures 112 are slightly misaligned thereby slightly decreasing the effective size of the apertures 112, slightly increasing resistance to outflow and slightly decreasing flow rate through the mixing chamber 109. In FIGS. 6F and 6F', the dial 110 is set in a third position (labeled as Position C) and the apertures 112 are substantially misaligned thereby substantially decreasing the effective size of the apertures 112, substantially increasing resistance to outflow and substantially decreasing flow rate through the mixing chamber 109. These particular settings (A, B and C) are for illustration only. Those of skill in the art will appreciate that the number of settings and the incremental changes in flow rate between settings may vary and in some embodiments the available settings may even provide for a complete blockage of flow through the mixing chamber 109 when so desired. Also, although in the example shown the degree of alignment or misalignment of apertures 112 determines the resistance to flow, other embodiments of this invention may be constructed wherein apertures are formed in specific patterns or at specific locations in the flow rate adjustor 108 and underlying downstream telescoping tube member 106b and the amount of flow resistance provided may be determined by the number of apertures that are aligned at any given point in time. As those of skill in the art will appreciate, in addition to these enumerated examples, various other designs or apparatus may also be used to allow the operator to adjust the resistance to flow into or through the mixing chamber 108, as desired.

Figure 7:
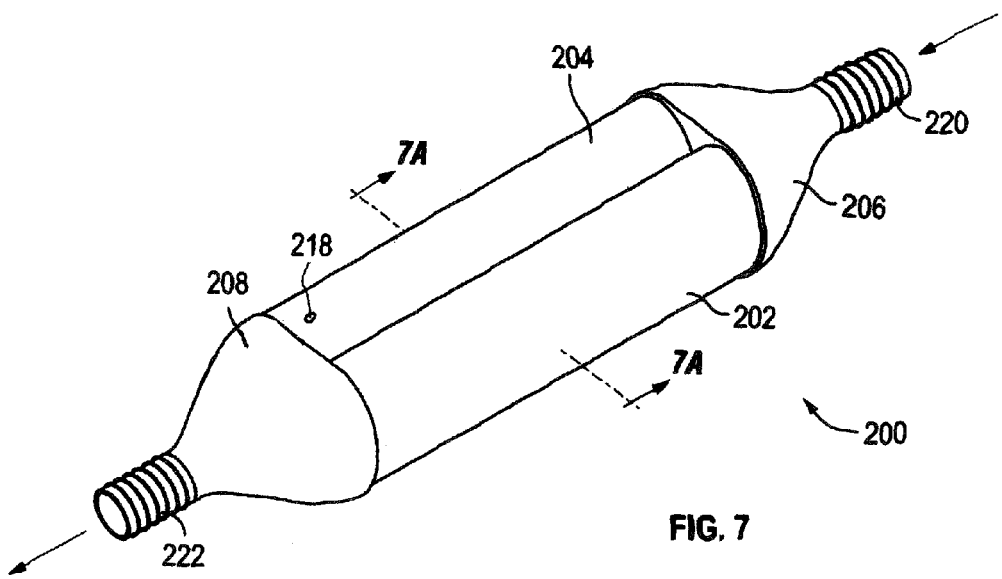
FIG. 7 is a perspective view of another embodiment of a bymixer device of the present invention.
Figure 7A:
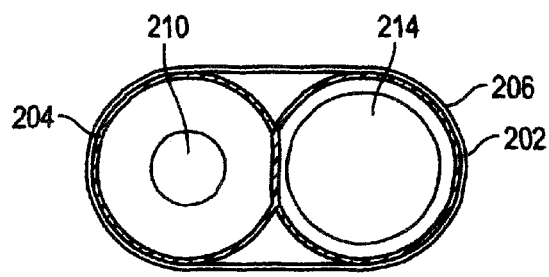
FIG. 7A is a cross sectional view through line 7A-7A of FIG. 7.
Figure 7B:
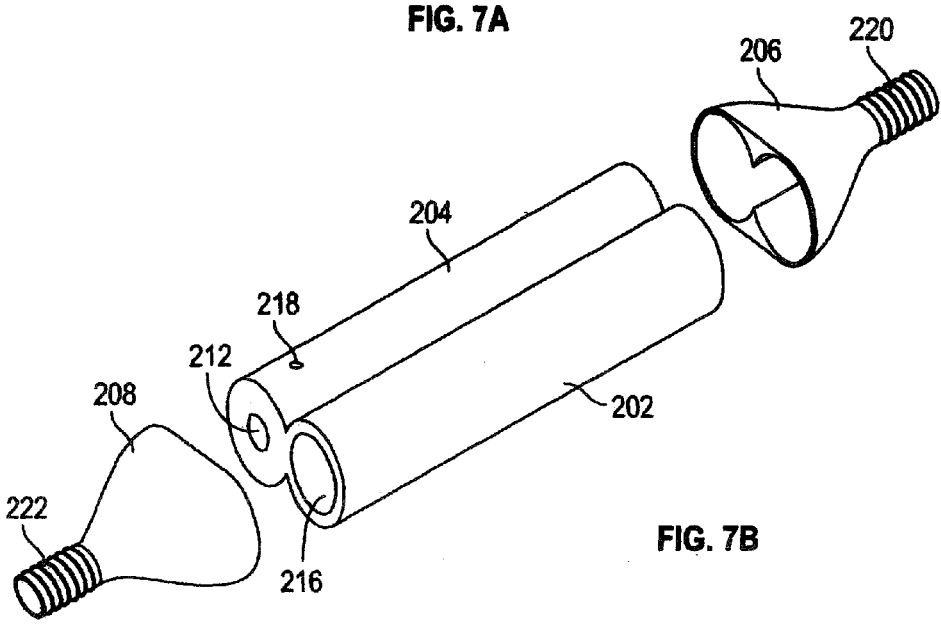
FIG. 7B is an exploded assembly view of the bymixer device of FIG. 7.
Figure 7C:
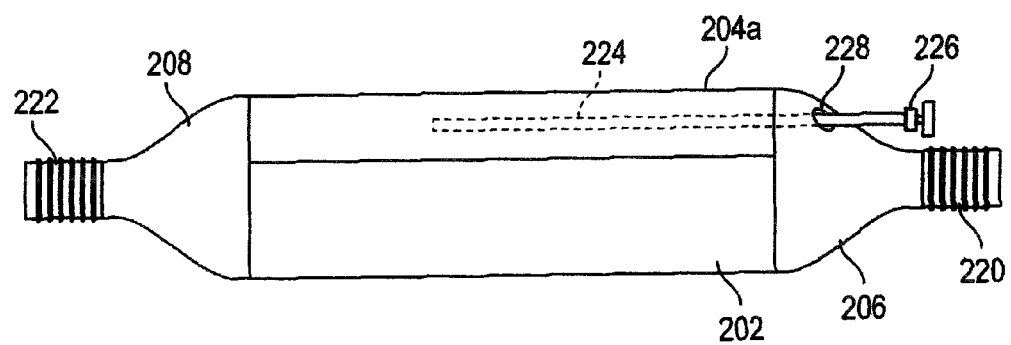
FIG. 7C is a side view of another embodiment of a bymixer device of the present invention adapted for insertion of a space occupying member into the mixing chamber to vary the volume of the mixing chamber.
Figure 7D:
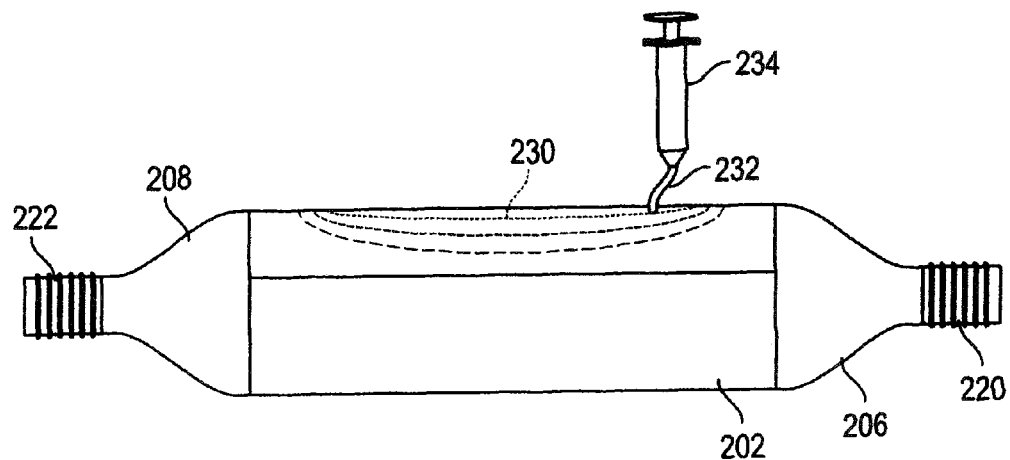
FIG. 7D is a side view of another embodiment of a bymixer device of the present invention having an inflatable bladder for varying the volume of the mixing chamber.

FIGS. 7 through 7D show other embodiments of bymixer devices of the present invention constructed generally of adjacently located tubes or luminal structures. Specifically, FIG. 7 shows a bymixer device 200 that comprises a first tube member 202, a second tube member 204, an inflow end cap member 206 and an outflow end cap member 208. In this device 200, the main flow channel 214 is the lumen of the first tube member 202 and the mixing chamber 212 is the lumen of the second tube member 204. The diameter of the mixing chamber 212, or alternatively the size of opening(s) into and/or out of the mixing chamber 212 will determine the fractional volume of gas that enters and passes through the mixing chamber 212. Inflow gas enters the inlet 220 of this bymixer device 200 and the gas flow is divided into the main flow channel 214 and the mixing chamber 212. At the end of the main channel 214 and the mixing chamber 212, the gas flows recombine in the outflow end cap member 208 and pass through the outlet 222 of the bymixer device 200. The tube members 202, 204 may be formed of separate tubes (e.g., two tubes positioned side by side and held together by end cap members 206, 208), separate tubes that are connected to each other (e.g., by adhesive or heat fusing) or a single sturcure (e.g., a dual lumen extrusion or unitary structure that essentially forms two tubes sharing a common wall). A sampling port 218 is provided at the lower downstream portion of the bymixer mixing chamber 212 to allow sampling of mixed gas fractions as described above.

The tube mambers 202, 204 may be of the same or different diameters. In some constructions of this bymixer device 200, the lumens of the tube mambers 202, 204 may be sized to provide for entry of the desired amount or flow of gas into the mixing chamber. In other constructions, the lumens of the tube members 202, 204 may be of the same size and restrictor member(s) such as partial closures, end caps with apertures in them or tube members may be inserted into or mounted on one or both ends of one or both of the tube members 202, 204 to provide a small hole for gas entry into and/or exit from the mixing chamber 212. Varying the size of this hole will result in variable resistance to gas flow from the inlet into the mixing chamber.

As illustrated in FIG. 7, in some embodiments, an optional insert 221 may be used to vary the proportional amount of gas that flows into the mixing chamber. This insert 221 comprises a tubular body having a pointed distal end with a mixing chamber opening 223 on one side and a main flow channel opening 225 on the other side. This insert is inserted into the end of the inlet 220 and advanced to a position where gas which exits through the mixing chamber opening 223 will enter the mixing chamber 212 and gas which exits through the main flow channel opening 225 will enter the main flow channel 214. Optionally, a plastic ridge (not shown) may run longitudinally on the outer surface of the insert 221 and such plastic ridge may mate with a groove (not shown) on the inner wall of the circumference of the bymixer inlet 220 to ensure proper rotational orientation of the insert 221 such that the mixing chamber opening 223 will match up with the entry of the mixing chamber 212 and the main flow channel opening 225 will match up with the entry of the main flow channel 214. A plurality of these inserts 221 may be provided with different sizing(s) of the mixing chamber opening 223 and/or main flow channel opening 225, which allow for a range of airflow resistances into the bymixer chamber. In this manner, the relative amount of gas entering the mixing chamber 212 may be varied by exchanging one inset 221 for another.

FIGS. 7C and 7D show variations of the device of FIG. 7 which incorporate different mechanisms for varying the effective internal volume of the mixing chamber 212. In FIG. 7C, an opening 228 is formed in the upstream end of the device to permit insertion of a space occupying member 224, such as a rod or tube, into the interior of the mixing chamber, thereby reducing the volume of gas that may collect in the mixing chamber. A plurality of different space occupying members 224 of differing length and/or diameter may be provided and a user may then vary the volume content of the mixing chamber by inserting different ones of the space occupying members 224. In FIG. 7D, a collapsible bladder 230 is attached lengthwise to one side of the inner circumference of the mixing chamber or otherwise disposed within the mixing chamber such that expansion (e.g., inflation) of the bladder 230 will reduce the volume of gas that may collect in the mixing chamber and retraction (e.g., deflation) of the bladder 230 will increase the volume of gas that may collect in the mixing chamber. In the example shown the bladder 230 is expanded and retracted by inflation and deflation using a syringe 234 or other inflation device attached to an inflation tube 232. In this manner, variable amounts of air or other fluid can be introduced into the bladder 230. A stopcock (not shown) or other valving member may be provided on tube 232 or on the bymixer device itself to prevent unwanted escape of inflation fluid from the bladder 230. Varying the amount of inflation fluid in this collapsible bladder 230 effects an infinite range of effective volume of the bymixer chamber.

In some applications, the bymixer devices of the present invention may have a fixed volume mixing chamber and a set resistance to gas flow into or through the mixing chamber. For such applications, the bymixer devices of this invention may be manufactured with a set volume of the mixing chamber 46, 109, 212 and a set resistance between the main channel 42, 111, 214 and the mixing chamber 46, 109, 212 and without the optional apparatus used for flow or volume adjustment apparatus (including but not limited to 44, 108, 221, 224 or 230). In this regard, it is to be appreciated that the mixing chamber volume and flow adjustability features are optional and/or may be provided independently of one another. For example, in some embodiments, the bymixer devices described in this patent application may be devoid of any adjustability of the mixing chamber volume or flow. In other embodiments, the volume of the mixing chamber may be adjustable but the flow rate into or through the mixing chamber may not be adjustable. In other embodiments, the flow rate into or through the mixing chamber may be adjustable and the volume of the mixing chamber may be non-adjustable. In other embodiments both the volume of the mixing chamber and the flow rate into or through the mixing chamber may be adjustable.

Advanced Data Processing and Displays for Applications of the Bymixer in Indirect Calorimetry The bymixer devices of the present invention can be used to determine mixed inspired gas concentrations and mixed expired gas concentrations of oxygen and carbon dioxide. With these measurements, along with the measurement of gas flow, the determinations of airway oxygen uptake per breath ($V_{O_2}$,br) and carbon dioxide elimination per breath ($V_{CO_2}$,br) can be made. However, these airway measurements of $\dot{V}_{O_2}$ (=$V_{O_2}$,br×f) and $\dot{V}_{CO_2}$ (=$V_{CO_2}$,br×f) only reflect the tissue values if patient ventilation is stable. When minute ventilation (the product of respiratory frequency, f, and tidal volume) changes, there will be a period of non-steady-state, with uncoupling of the airway and tissue values of $\dot{V}_{O_2}$ and $\dot{V}_{CO_2}$.

During the measurement of airway $\dot{V}_{O_2}$ and $\dot{V}_{CO_2}$, the values of airway flow can also generate the measurement of tidal volume. With this measurement, we can constrain the values of airway $\dot{V}_{O_2}$ and $\dot{V}_{CO_2}$ to represent the tissue values by correcting for changes in minute ventilation using our mammalian non-steady state computer model of gas kinetics in the body.

These calculations can be conducted in real time by a series of computer algorithms and incorporated into a microprocessor to provide corrected measurements of $\dot{V}_{O_2}$ and $\dot{V}_{CO_2}$ at the patient bedside. A monitor display, with appropriate alerts and alarms for the clinician, can be incorporated into this measurement system.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A bymixer device connectable to a patient ventilation conduit and useable for sampling, sensing or analyzing mixed expired gasses from a plurality of the patient's consecutive breaths, said device comprising:
   an inflow port connectable to the patient ventilation conduit such that expired gases from a plurality of consecutive breaths enter the inflow port;
   a main flow channel;
   a mixing chamber having a hollow inner gas accumulation space of adjustable volume;
   an outflow port;
   means for sampling, sensing or analyzing mixed expired gasses from the hollow inner gas accumulation space of the mixing chamber; and
   apparatus for adjusting the volume of the hollow inner gas accumulation space of the mixing chamber;
   said bymixer device being constructed such that i) most of the gas which enters the inflow port will pass into the main flow channel; ii) a portion of the gas which enters the inflow port will pass into the mixing chamber such that expired gasses from a plurality of consecutive breaths accumulate in the hollow inner gas accumulation space of the mixing chamber and iii) gasses that exit the main flow channel and mixing chamber will subsequently flow out of the outflow port.

2. A device according to claim 1 wherein the apparatus for adjusting the volume of the hollow inner gas accumulation space of the mixing chamber comprises apparatus for adjusting the size of the mixing chamber.

3. A device according to claim 1 wherein the apparatus for adjusting the volume of the mixing chamber comprises at least one space occupying member that is positionable within the mixing chamber.

4. A device according to claim 3 wherein said at least one space occupying member comprises a plurality of space occupying members of differing size.

5. A device according to claim 1 wherein the apparatus for adjusting the volume of the mixing chamber comprises an expandable bladder.

6. A device according to claim 5 wherein the bladder is inflatable and wherein the device further comprises an inflator for inflating the bladder.

7. A device according to claim 1 wherein the mixing chamber flow is adjustable and wherein the device further comprises apparatus for adjusting the flow of gas into or through the mixing chamber.

8. A device according to claim 7 wherein the apparatus for adjusting the flow of gas into or through the mixing chamber comprises a flow restrictor.

9. A device according to claim 8 wherein the flow restrictor comprises a variable flow blocker which fully or partially blocks one or more apertures through which gas flows into or out of the mixing chamber.

10. A device according to claim 8 wherein the adjustable flow restrictor comprises at least one removable insert that modifies the resistance to gas flow.

11. A device according to claim 10 wherein said at least one removable insert comprises a plurality of inserts each having a different sized aperture through which gas flows into or out of the mixing chamber.

12. A device according to claim 1 wherein the means for sampling, sensing or analyzing mixed expired gasses from the hollow inner gas accumulation space of the mixing chamber comprises a sampling port.

13. A device according to claim 1 wherein the means for sampling, sensing or analyzing mixed expired gasses from the hollow inner gas accumulation space of the mixing chamber comprises a sensor.

14. A device according to claim 1 wherein the means for sampling, sensing or analyzing mixed expired gasses from the hollow inner gas accumulation space of the mixing chamber comprises a sampling port and wherein the device further comprises an analyzer connected to the sampling port to analyze one or more variables in gas samples from the hollow inner gas accumulation space via the sampling port.

15. A bymixer device for in-line connection to a respiratory gas flow conduit and usable for sampling, sensing or analyzing mixed expired gasses from a plurality of the patient's consecutive breaths, said bymixer device comprising:
- a shell having a hollow mixing chamber cavity therewithin;
- a tube extending through the hollow mixing chamber cavity, said tube having a lumen that defines a main flow channel, an inlet end of the tube being connectable to the respiratory conduit such that gas from the respiratory flow conduit flows into the inlet end of the tube and an outlet end of the tube being connectable to the respiratory conduit such that gas from the outlet end of the tube flows into the respiratory flow conduit;
- at least one opening near the inflow end of the tube through which a portion of the gas flowing through the main flow channel will pass into the hollow mixing chamber;
- at least one opening near the outflow end of the tube through which gas will pass from the mixing chamber back into the main flow channel; and
- means for sampling, sensing or analyzing mixed expired gasses from the hollow mixing chamber cavity.

16. A device according to claim 15 wherein the mixing chamber volume is adjustable.

17. A device according to claim 16 wherein the shell comprises first and second shell portions and wherein the volume of the mixing chamber is adjustable by moving one or both of the first and second shell portions to increase or decrease the size of the mixing chamber.

18. A device according to claim 15 wherein flow though mixing chamber is adjustable.

19. A device according to claim 18 wherein flow through the mixing chamber is adjustable by changing the alignment or misalignment of one or more apertures through which gas flows into or out of the mixing chamber.

20. A bymixer device for in-line connection to a respiratory gas flow conduit, said
bymixer device comprising:
- a first tube member having an inflow end, an outflow end and a lumen which defines a main flow channel;
- a second tube member having an inflow end, an outflow end and a lumen which defines a hollow mixing chamber;
- an inflow end cap member connected to the inflow ends of the first and second tube members and connectable to a first location on the respiratory gas flow conduit; and
- an outflow end cap member connected to the outflow ends of the first and second tube members and connectable to a second location on the respiratory gas flow conduit;
- said device being configured such that most of the gas that enters the inflow end cap member subsequently flows into the main flow channel, a fraction of the gas that enters the inflow end cap member subsequently flows into the mixing chamber and gas that exits the main flow channel and mixing chamber becomes recombined and delivered back into the respiratory gas flow conduit by the outflow end cap member;
- wherein the volume of the mixing chamber is variable; and
- wherein the device further comprises means for sampling, sensing or analyzing mixed expired gasses from the hollow mixing chamber.

21. A device according to claim 20 wherein the fraction of gas that enters the mixing chamber is fixed.

22. A device according to claim 20 wherein the fraction of gas that enters the mixing chamber is variable.

23. A device according to claim 20 further comprising a one or more inserts insertable into the device, each of said inserts being constructed to cause a desired fraction of gas to flow into the mixing chamber.

24. A device according to claim 23 wherein each of the inserts is insertable into the inflow end cap member and has a first aperture through which gas flows into the main flow channel and a second aperture through which gas flows into the mixing chamber, the relative sizes of the first and second apertures being determinative of the respective fractions of gas that enter the main flow channel and mixing chamber.

25. A device according to claim 20 further comprising one or more space occupying members insertable into the mixing chamber to change the volume of the mixing chamber.

26. A device according to claim 20 further comprising an expandable bladder the expansion of which changes the volume of the mixing chamber.

27. A device according to any of claim 1, 15 or 20 wherein the means for sampling, sensing or analyzing mixed expired gasses from the hollow inner gas accumulation space of the mixing chamber comprises a sampling port.

28. A device according to any of claim 1, 15 or 20 wherein the means for sampling, sensing or analyzing mixed expired gasses from the hollow inner gas accumulation space of the mixing chamber comprises a sensor.

29. A device according to any of claim 1, 15 or 20 wherein the means for sampling, sensing or analyzing mixed expired gasses from the hollow inner gas accumulation space of the mixing chamber comprises a sampling port and wherein the device further comprises a monitoring apparatus connected to the sampling port to analyze, measure or otherwise determine one or more variables from gas sampled from the hollow inner gas accumulation space via the sampling port.

30. A device according to claim 29 wherein said one or more variables comprises a variable selected from: volume-averaged alveolar $PCO_2$ ($P_{AE_{CO_2}}$); pulmonary carbon dioxide elimination ($\dot{V}_{CO_2}$); pulmonary oxygen uptake ($\dot{V}_{O_2}$); pulmonary carbon dioxide elimination per breath ($V_{CO_2,br}$); pulmonary oxygen uptake per breath ($V_{O_2,br}$); concentration or partial pressure of volatile gases and concentration or partial pressure of non-volatile gasses.

31. A device according to claim 29 wherein the monitoring apparatus comprises a computer, microprocessor or other calculating apparatus that is programmed to additionally calculate one or more calculated values based on said one or more variable.

32. A device according to claim 31 wherein the monitoring apparatus is adapted to receive input data and to use the input data, along with said at least one variable, to calculate a calculated value of interest.

33. A device according to claim 32 wherein the monitoring apparatus is adapted to receive input data selected from: body weight, barometric pressure, airway opening gas humidity; airway opening gas temperature and airway opening gas flow.

34. A device according to claim 32 wherein the monitoring apparatus is adapted to calculate a value of interest selected from: pulmonary carbon dioxide elimination ($\dot{V}_{CO_2}$), pulmonary carbon dioxide elimination per breath ($V_{CO_2,br}$), pulmonary oxygen uptake ($\dot{V}_{O_2}$), pulmonary oxygen uptake per breath ($V_{O_2,br}$), minute ventilation ($\dot{V}_E$), tidal volume ($V_T$), vital capacity (VC), peak inspiratory pressure, end tidal $CO_2$, expired $O_2$, inspired $O_2$, $CO_2$ elimination, $\dot{V}_{CO_2}$, and $O_2$ uptake, $\dot{V}_{O_2}$, tidal volume, minute volume, airway pressure, airway compliance, estimated energy required (EER) and respiratory quotient (RQ).

35. A method for sampling mixed respiratory gas from a respiratory ventilation circuit:
A. providing a bymixer device that comprises an inflow port, a main flow channel, a mixing chamber and an outflow port, said bymixer device being constructed such that i) most of the gas which enters the inflow port will pass into the main channel; ii) a portion of the gas which enters the inflow port will pass into the mixing chamber, iii) gasses that exit the main flow channel and mixing chamber will subsequently flow out of the outflow port and iv) gasses from a plurality of consecutive breaths will become mixed within the mixing chamber;

B. attaching the inflow port of the bymixer device to the ventilation circuit at a first location;

C. attaching the outflow port of the bymixer device to the ventilation circuit at a second location;

D. selecting or adjusting at least one of i) the internal volume of the mixing chamber and ii) the resistance to flow into or through the mixing chamber; and E. sampling or obtaining data from respiratory gases that have become mixed within the mixing chamber.

36. A method according to claim 35 wherein Step E comprises withdrawing a sample from the mixing chamber and obtaining data from the withdrawn sample.

37. A method according to claim 35 wherein Step E comprises positioning a sensor within the mixing chamber and obtaining data from gasses within the mixing chamber by way of said sensor.

38. A method according to claim 35 further comprising the step of calculating a variable based on data obtained in Step E.

39. A method according to claim 35 wherein Step E comprises performing capnography on respiratory gases that have become mixed within the mixing chamber.

40. A method according to claim 35 wherein Step E comprises performing calorimetry on respiratory gases that have become mixed within the mixing chamber.

41. A method according to claim 25 wherein data obtained in Step E comprises or is used to calculate at least one variable selected from the group consisting of:
volume-averaged alveolar $PCO_2 (P_{AECO2})$,
pulmonary carbon dioxide elimination ($\dot{V}_{CO2}$);
pulmonary oxygen uptake CVO2);
pulmonary carbon dioxide elimination per breath ($V_{CO2,br}$)
pulmonary oxygen uptake per breath ($V_{O2,br}$)
concentration or partial pressure of volatile gases; and
concentration or partial pressure of non-volatile gasses.

42. A method according to claim 25 further comprising the step of determining one or more values selected from the group consisting of:
minute ventilation (VE);
tidal volume ($V_T$);
Total Lung Capacity (TLC);
Functional Residual Capacity (FRC); and
Vital Capacity (VC).

43. A method according to claim 25 wherein the size of the mixing chamber is variable and wherein Step D comprises changing the size of the mixing chamber.

44. A method according to claim 25 wherein the resistance to flow into or through the mixing chamber is variable and wherein Step D comprises changing the resistance to flow into or through the mixing chamber.

* * * * *